(12) United States Patent
Nekhai et al.

(10) Patent No.: US 9,447,047 B2
(45) Date of Patent: Sep. 20, 2016

(54) INHIBITORS OF PROTEIN PHOSPHATASE-1 AND USES THEREOF

(71) Applicants: Sergei Nekhai, McLean, VA (US); Alexander Bukreyev, League City, TX (US)

(72) Inventors: Sergei Nekhai, McLean, VA (US); Alexander Bukreyev, League City, TX (US)

(73) Assignees: Howard University, Washington, DC (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/421,757

(22) PCT Filed: Mar. 14, 2013

(86) PCT No.: PCT/US2013/031659
§ 371 (c)(1),
(2) Date: Feb. 13, 2015

(87) PCT Pub. No.: WO2014/028051
PCT Pub. Date: Feb. 20, 2014

(65) Prior Publication Data
US 2016/0024013 A1    Jan. 28, 2016

Related U.S. Application Data

(60) Provisional application No. 61/682,952, filed on Aug. 14, 2012.

(51) Int. Cl.
| | |
|---|---|
| *A61K 31/47* | (2006.01) |
| *C07D 219/04* | (2006.01) |
| *A61K 31/473* | (2006.01) |
| *C07D 221/16* | (2006.01) |
| *C07D 409/06* | (2006.01) |
| *C07D 417/12* | (2006.01) |

(52) U.S. Cl.
CPC ........... *C07D 219/04* (2013.01); *A61K 31/473* (2013.01); *C07D 221/16* (2013.01); *C07D 409/06* (2013.01); *C07D 417/12* (2013.01)

(58) Field of Classification Search
USPC .......................................... 514/311; 546/104
See application file for complete search history.

(56) References Cited

U.S. PATENT DOCUMENTS 8,278,326 B2 * 10/2012 Nekhai ................ C07D 219/04
514/311

OTHER PUBLICATIONS

PubChem CID-4543166 (create date Sep. 15, 2005).
Modrof et al., The Journal of Biological Chemistry, 277(36):33099-33104 (Sep. 2, 2002).

* cited by examiner

*Primary Examiner* — Rei-Tsang Shiao
(74) *Attorney, Agent, or Firm* — Fitch, Even, Tabin & Flannery LLP

(57) ABSTRACT

Inhibitors of protein phosphatase-1 (PP-1) and their use in a method for the treatment or prevention of viral infections caused by HIV or ebola virus are disclosed. Inhibitors of protein phosphatase-1 in effective amounts have been shown to slow down viral replication upon contacting ebola virus or cells containing the ebola virus.

12 Claims, 20 Drawing Sheets

Figure 2:
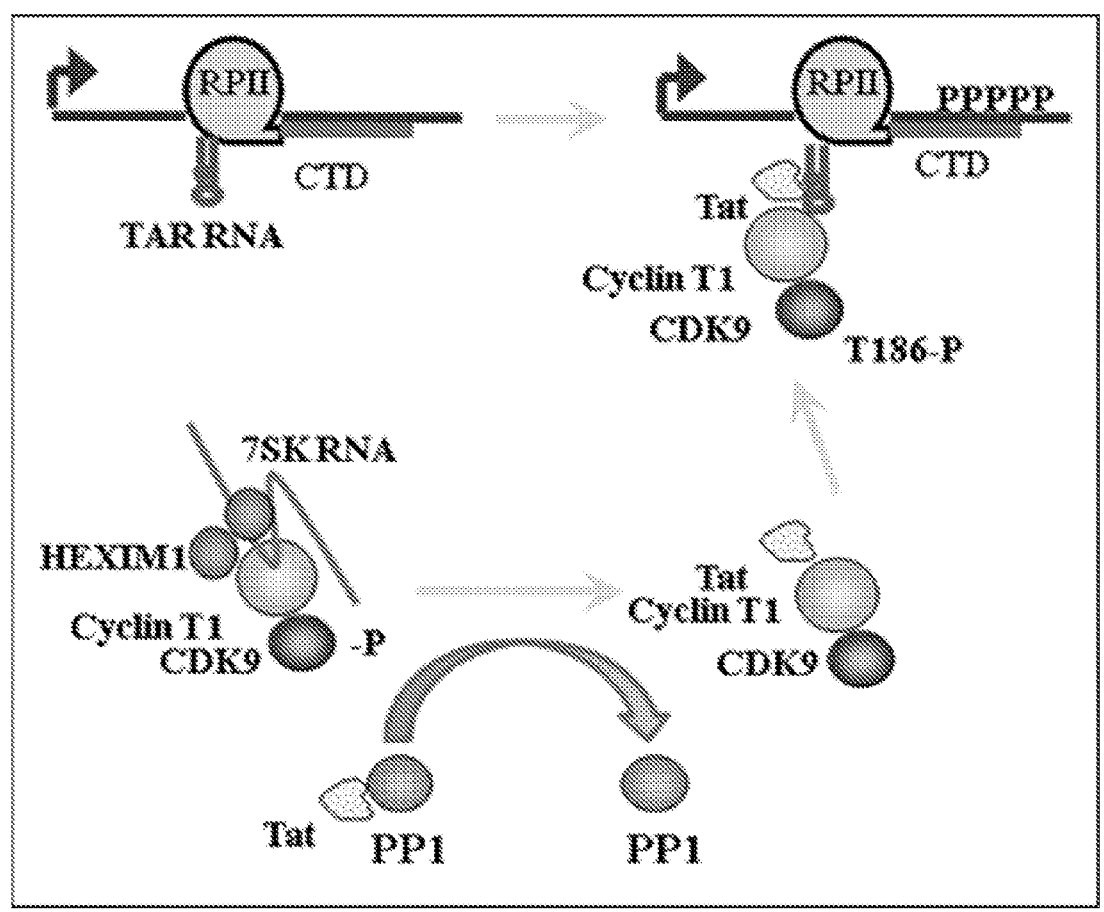

```
                                     29-31          42-46      52
EBOV Zaire        MEASYERGRPPAARQHSRDGHDHHVRARSSSRENYRGEYRQSRSASQVRVPIVFHKYRVE 60
EBOV Sudan        MERGRERGRSRNSRADQQNSTGPQFRTRSISRDKTTTDYRSSRSTSQVRVPIVFHKKGTG 60
EBOV Bundibugyo   MDSFHERGRSRTIRQSARDGPSHQVRTRSSSRDSHRSEYHTPRSSSQVRVPIVFHRKTD 60
EBOV Ivory Coast  MEVVHERGRSPISRQNTRDGPSHLVPARSSSRASYRSEYHTPRSASQIRVPIVFHRKKTD 60
MARV              MQQPRGRSRTRNHQVTPTIYHETQLPSKPHYTNYHPRARSMSSTRSSAESSPTNHIPRAR 60
```

Fig. 1

| Description | Control | | +1H4 | |
|---|---|---|---|---|
| | Score | Coverage | Score | Coverage |
| enolase 1; phosphopyruvate hydratase; MYC promoter-binding protein 1; non-... | 94.51 | 30.76 % | 93.79 | 30.85 % |
| heat shock 70kDa protein 8 isoform 1; heat shock cognate protein, 71-kDa; he... | 94.03 | 26.78 % | 57.73 | 14.55 % |
| Heat shock 70 kDa protein 1 (HSP70.1) (HSP70-1/HSP70-2) | 91.64 | 25.27 % | 85.34 | 22.15 % |
| protein phosphatase 1, catalytic subunit, alpha isoform [Homo sapiens] | 59.05 | 19.70 % | 52.55 | 23.33 % |
| Beta 5-tubulin [Homo sapiens] | 56.08 | 27.83 % | 46.04 | 22.07 % |
| heat shock 90kDa protein 1, beta; heat shock 90kD protein 1, beta; Heat-shoc... | 52.52 | 15.19 % | 30.79 | 9.25 % |
| Tubulin alpha-1 chain (Alpha-tubulin 1) | 51.57 | 21.96 % | 52.09 | 24.83 % |
| nucleolin [Homo sapiens] | 46.31 | 14.80 % | 56.73 | 12.73 % |
| Similar to tubulin, beta, 2 [Homo sapiens] | 44.41 | 23.60 % | 38.20 | 15.96 % |
| heat shock 70kD protein 1-like [Homo sapiens] | 44.20 | 17.80 % | 40.66 | 11.54 % |
| heterogeneous nuclear ribonucleoprotein K [Mus musculus] | 41.78 | 19.87 % | 42.01 | 15.55 % |
| eukaryotic translation elongation factor 2; polypeptidyl-tRNA translocase [Hom... | 41.30 | 14.92 % | 64.14 | 17.95 % |
| Alpha enolase, lung specific (2-phospho-D-glycerate hydro-lyase) (Non-neural ... | 40.97 | 16.59 % | 43.30 | 13.76 % |
| heat shock 70kDa protein 2; heat shock 70kD protein 2; Heat-shock 70kD prot... | 38.19 | 14.24 % | 24.88 | 6.10 % |
| chaperonin containing TCP1, subunit 2 (beta); chaperonin containing t-comple... | 37.58 | 13.85 % | 25.02 | 16.45 % |
| tyrosine 3/tryptophan 5 -monooxygenase activation protein, zeta polypeptide;... | 35.73 | 20.41 % | 38.17 | 35.51 % |
| heat shock 90kDa protein 1, alpha; heat shock 90kD protein 1, alpha [Homo s... | 34.11 | 8.88 % | 34.16 | 6.28 % |
| phosphopyruvate hydratase (EC 4.2.1.11) beta - human | 33.68 | 16.13 % | 23.17 | 8.99 % |
| Pyruvate kinase, M2 isozyme | 33.30 | 12.99 % | 37.60 | 19.96 % |
| Similar to heterogeneous nuclear ribonucleoprotein U (scaffold attachment fac... | 29.68 | 15.25 % | 18.01 | 8.05 % |
| glyceraldehyde-3-phosphate dehydrogenase [Homo sapiens] | 29.30 | 17.91 % | 40.77 | 17.91 % |
| tyrosine 3/tryptophan 5 -monooxygenase activation protein, epsilon polypeptid... | 27.31 | 18.47 % | 44.37 | 23.53 % |
| neurone-specific enolase [Homo sapiens] | 27.01 | 15.70 % | 17.23 | 7.16 % |
| heat shock 70kDa protein 6 (HSP70B') [Homo sapiens] | 25.88 | 8.86 % | 18.13 | 4.51 % |
| similar to Heterogeneous nuclear ribonucleoprotein A1 (Helix-destabilizing prot... | 25.06 | 17.50 % | 13.97 | 11.86 % |
| Unknown (protein for MGC:9832) [Homo sapiens] | 24.63 | 17.22 % | 11.97 | 13.61 % |
| BiP protein [Homo sapiens] | 23.95 | 5.63 % | 11.39 | 3.29 % |
| eukaryotic translation elongation factor 1 alpha 1; CTCL tumor antigen; transla... | 23.63 | 22.73 % | 36.17 | 19.26 % |

Fig. 7

Effect of 1E7-03 on VP30 Phosphorylation and Cellular Distribution of PP1

Fig. 19

Fig. 20

SEQUENCE LISTING

```
<160> NUMBER OF SEQ ID NOS: 11

<210> SEQ ID NO 1
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: X
<222> LOCATION: (5)..(5)
<223> OTHER INFORMATION: Phosphorylated serine

<400> SEQUENCE: 1

His Ile Pro Arg Xaa Pro Tyr Lys Phe Pro Ser Ser Pro Leu Arg
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: peptide

<400> SEQUENCE: 2

Lys Lys Cys Cys Phe His Cys Gln Val Cys Phe Ile Thr Lys
1               5                   10
```

<210> SEQ ID NO 3
<211> LENGTH: 14
<212> TYPE: PRT
<213> ORGANISM: Artificial Sequence
<220> FEATURE:
<223> OTHER INFORMATION: peptide

<400> SEQUENCE: 3

Lys Arg Lys Arg Lys Asn Ser Arg Val Thr Phe Ser Glu Asp
1               5                   10

<210> SEQ ID NO 4
<211> LENGTH: 28
<212> TYPE: PRT
<213> ORGANISM: Artificial Sequence
<220> FEATURE:
<223> OTHER INFORMATION: peptide
<220> FEATURE:
<221> NAME/KEY: X
<222> LOCATION: (5)..(5)
<223> OTHER INFORMATION: Phosphorylated serine

<400> SEQUENCE: 4

His Ile Pro Arg Xaa Pro Tyr Lys Phe Pro Ser Ser Pro Leu Arg Ala
1               5                   10                  15

Ala Ala Ala Ala Ser Arg Ala Thr Ala Ser Glu Asp
            20                  25

<210> SEQ ID NO 5
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: X
<222> LOCATION: (5)..(5)
<223> OTHER INFORMATION: Phosphorylated serine

<400> SEQUENCE: 5

His Ile Pro Arg Xaa Pro Tyr Lys Phe Pro Ser Ser Pro Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: peptide

<400> SEQUENCE: 6

Lys Lys Cys Cys Phe His Cys Gln Ala Cys Ala Ile Thr Lys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: X
<222> LOCATION: (3)..(3)
<223> OTHER INFORMATION: Phosphorylated threonine

<400> SEQUENCE: 7

Lys Thr Thr Ile Arg Arg
1               5

```
<210> SEQ ID NO 8
<211> LENGTH: 15
<212> TYPE: PRT
<213> ORGANISM: Artificial Sequence
<220> FEATURE:
<223> OTHER INFORMATION: peptide

<400> SEQUENCE: 8

Arg Ala Pro Gln Asp Ser Gln Thr His Gln Ala Ser Leu Ser Lys
1               5                   10                  15

<210> SEQ ID NO 9
<211> LENGTH: 33
<212> TYPE: PRT
<213> ORGANISM: Artificial Sequence
<220> FEATURE:
<223> OTHER INFORMATION: peptide

<400> SEQUENCE: 9

Gly Pro Gln Gly Pro Gly Gly Gly Ile Asn Val Gln Glu Ile Leu
1               5                   10                  15

Thr Ser Ile Met Gly Ser Pro Asn Ser His Pro Ser Glu Glu Leu Leu
            20                  25                  30

Lys

<210> SEQ ID NO 10
<211> LENGTH: 18
<212> TYPE: PRT
<213> ORGANISM: Artificial Sequence
<220> FEATURE:
<223> OTHER INFORMATION: peptide

<400> SEQUENCE: 10

Val Phe Leu Ile Asp Leu Asn Ser Thr His Gly Thr Phe Leu Gly His
1               5                   10                  15

Ile Arg

<210> SEQ ID NO 11
<211> LENGTH: 9
<212> TYPE: PRT
<213> ORGANISM: Artificial Sequence
<220> FEATURE:
<223> OTHER INFORMATION: peptide

<400> SEQUENCE: 11

Leu Asn Leu Asp Ser Ile Ile Gly Arg
1               5
```

INHIBITORS OF PROTEIN PHOSPHATASE-1 AND USES THEREOF

This application claims the benefit of U.S. Provisional Application Ser. No. 61/682,952, filed Aug. 14, 2012 which is incorporated herein as if fully rewritten.

The present application relates to inhibitors of Protein Phosphatase-1 and medical uses of such inhibitors. More specifically, a class of compounds is provided that inhibit PP-1. Further, methods to use PP-1 inhibitors for treating Ebola viral infection are described.

BACKGROUND

The family Filoviridae, which includes Marburg virus and five species of Ebola virus (EBOV), four of which are Zaire, Sudan, Ivory Coast and Bundibugyo (Towner, J. S., et al., *Newly discovered ebola virus associated with hemorrhagic fever outbreak in Uganda.* PLoS Pathog, 2008. 4(11): p. e1000212), causes severe hemorrhagic fever in humans, with a lethality of up to 90%. Outbreaks of Ebola (EBOV) and Marburg (MARV) infections occur in Central Africa on a regular basis (Groseth, A., H. Feldmann, and J. E. Strong, *The ecology of Ebola virus.* Trends Microbiol, 2007. 15(9): p. 408-16). Sequences of EBOV Zaire identified in wild apes during the 2003-2005 outbreaks in Gabon and The Democratic Republic of Congo (DRC) demonstrated circulation of several lineages of the virus and recombination events between the viruses (Wittmann, T. J., et al., Isolates of Zaire ebolavirus from wild apes reveal genetic lineage and recombinants. Proc Natl Acad Sci USA, 2007. 104(43): p. 17123-7). Similarly, sequence analysis of MARV isolated during the 1999 outbreak in the DRC demonstrated the simultaneous circulation of multiple genetic lineages with up to 21% nucleotide divergence (Towner, J. S., et al., Marburgvirus genomics and association with a large hemorrhagic fever outbreak in Angola. J Virol, 2006. 80(13): p. 6497-516; Bausch, D. G., et al., *Marburg hemorrhagic fever associated with multiple genetic lineages of virus.* N Engl J Med, 2006. 355(9): p. 909-19). Sequence analysis of multiple MARV isolates in bats collected during the 2007 outbreak also demonstrated the simultaneous circulation of multiple diverse lineages of the virus, including those identical or almost identical to human isolates (Towner, J. S., et al., *Isolation of genetically diverse Marburg viruses from Egyptian fruit bats.* PLoS Pathog, 2009. 5(7): p. e1000536). These data suggest a broad distribution and significant diversity of filoviruses. There is an urgent need for development of treatments against filoviruses.

SUMMARY

Compounds are provided that may be used to treat, inhibit and/or prevent EBOV infection. Without being bound by any theory, it is believed that the compounds inhibit dephosphorylation of transcription elongation factor VP30 (a viral protein) encoded by the EBOV genome. U.S. Pat. No. 8,278,326 to Nekhai et al. describes compounds which target phosphatase-1 (PP1) and their use to inhibit the replication of the pathogenic HIV-1 virus. PP1 comprises a major class of eukaryotic protein serine/threonine phosphatases that regulate a wide range of cellular functions. VP30 is dephosphorylated by PP1, and the de-phosphorylated form of VP30 is vital for EBOV transcription and replication. Modrof, J., et al., *Phosphorylation of VP30 impairs ebola virus transcription*, J Biol Chem, 277(36): 33099-104 (2002). It has been surprisingly found that PP1 also plays a role in the replication of EBOV and that PP1 inhibits EBOV replication by blocking the interaction of EBOV VP30 with PP1. Surprisingly using the compounds described herein, the viral protein VP30 will remain phosphorylated and the viral polymerase will remain in a transcriptionally inactive form. As a result, replication of the virus will be blocked.

The discovery that targeting PP1 with the compounds described herein can inhibit transcription and replication of EBOV is surprising because the mechanism of replication of EBOV and HIV-1 are very different. HIV-1 and EBOV use different viral proteins and different host proteins to replicate. The HIV-1 virus is relatively less contagious, with a long incubation period (as a chronic disease), and primarily infects T-lymphocytes of a mammalian system. The HIV-1 virus destroys T-lymphocytes, thereby adversely impacting the immune system, and mutates at a high rate during replication. In contrast, the EBOV primarily infects endothelial cells, mononuclear phagocytes, and hepatocytes, has a relatively short incubation period, is extremely contagious, and its genes are highly conserved during replication. Yet, surprisingly PP1 regulates transcription and replication of both HIV-1 and EBOV and surprising the compounds described herein inhibit the regulation of PP1. The compounds described herein can be used to inhibit dephosphorylation of VP30 viral protein present in EBOV by blocking the action of PP1 with EBOV VP30. While PP1 is a complex dimer enzyme participating in a wide range of cellular functions, there has been no reason to believe that compounds effective to inhibit HIV-1 replication would also be effective to inhibit EBOV replication. Also a number of compounds described herein have been discovered to inhibit the replication of HIV virus or a cell containing the HIV virus.

In one aspect, described herein are methods of inhibiting replication of EBOV with the compounds of general formula I and other compounds having the structures illustrated herein. Methods for treating a subject infected with or at risk of infection with Ebola with the compounds of general formula I and other compounds described herein. The methods include various routes of administration for the compounds of formula (I) and other compounds described herein, as well as use of compounds of formula (I) and other compounds in combination with other therapeutic agents effective for the treatment or prevention of EBOV infections.

While not intending to be limited by theory, it is presently believed that the small molecule compounds described herein surprisingly target a non-catalytic site or sites in PP1 needed for the binding of PP1 regulatory subunits of the EBOV virus. This prevents interaction of PP1 with viral targets such as VP30 or a VP30-interacting PP1-targeting subunit and suppresses EBOV replication without exhibiting cellular toxicity.

By one approach, the low micromolar $IC_{50}$ for these compounds effective to inhibit EBOV replication and lack of cellular toxicity indicates their usefulness as anti-Filoviridae, in particular anti-EBOV, therapeutics.

In one aspect, compounds of Formula (I) are provided, where Formula (I) is:

(I)

wherein n is 1 or 2;
Ar is phenyl or thienyl, and is optionally substituted;
each $R^1$ is independently $R^6$, $C(O)R^6$, $C(O)$—$OR^6$, or $C(O)N(R^6)_2$;
$R^2$ is H or optionally substituted C1-C6 alkyl, or a group of formula —$C(O)NH$—$R^1$;
$R^3$ is independently at each occurrence selected from halo, $NO_2$, CN, R, OR, $NR_2$;
$S(O)_qR$, COOR, and $CONR_2$, where each R is independently H, C1-C4 alkyl, or C1-C4 haloalkyl;
m is 0-4;
$R^4$ is $R^6$, halo, =O, $COOR^6$, $CON(R^6)_2$, $S(O)_qR^6$, $N(R^6)_2$, or $OR^6$;
p is 0-2;
each q is independently 0-2;
Z is O or $NR^5$;
$R^5$ is $R^6$ or $C(O)R^6$; and
$R^6$ is independently at each occurrence selected from H, C1-C6 alkyl, C5-C6 aryl, and (C5-C6-aryl)-C1-C6 alkyl, where each alkyl and aryl is optionally substituted; provided that n is 2 when Z is O and Ar represents para-halophenyl; or a pharmaceutically acceptable salt thereof.

Pharmaceutical compositions are provided that include at least one compound of formula (I) or other compound described herein admixed with a pharmaceutically acceptable excipient. The use of the compounds of formula (I) and other compounds described herein for manufacture of a medicament, especially a medicament for the treatment of Ebola infected subjects, is provided.

In another aspect, methods are provided to treat, inhibit and/or prevent an Ebola infection by administering to a subject in need thereof a compound of formula (I) and other compounds described herein in an amount effective to mitigate the effects, inhibit or prevent EBOV infections. The methods include various routes of administration for the compounds of formula (I) and other compounds described herein as well as use of a compound of formula (I) in combination with other therapeutic agents effective for the treatment, inhibition, or prevention of Ebola infections.

BRIEF DESCRIPTION OF THE DRAWINGS

FIG. 1 illustrates a comparison of phosphorylation sites of VP30 of various species of filoviruses (clustal W2 alignment of N-termini of the proteins). The phosphorylated serine (S) and threonine (T) residues of EBOV Zaire, MARV, and the putative phosphorylated residues of additional species of EBOV are underlined.

FIG. 2 illustrates a schematic representation of the PP1 role in HIV-1 transcription activation.

FIG. 3 illustrates four binding modes for PP1 inhibitors: (1) compounds positioned toward Tyr 255; (2) compounds reach Asp 166; (3) compounds span toward Gln 262; and (4) compounds which form more than 4 hydrogen bonds with PP1.

FIG. 4 A through FIG. 4D illustrate that 1H4 compound competes with RVxF motif. FIG. 4 A illustrates that 1H4 inhibits kinetics of pRb-Tat peptide dephosphorylation by PP1α. FIG. 4 B illustrates that 1H4 inhibits kinetics of pRb-cdNIPP dephosphorylation by PP1α. FIG. 4C and FIG. 4 D illustrate that 1H4 competitively inhibits pRb-Tat peptide dephosphorylation by PP1α.

FIG. 5 illustrates 1H4 has no effect on PP1 enzymatic activity. FIG. 5 A illustrates that 1H4 has no effect on the kinetics of KT(pT)IRR (SEQ ID NO: 7) peptide dephosphorylation by PP1α. FIGS. 5 B and 5 C illustrate that 1H4 has no effect on Km and VMAX of KT(pT)IRR (SEQ ID NO: 7) peptide dephosphorylation by PP1α.

FIGS. 6 A and 6 B illustrate that 1H4 prevents the interaction of Tat with PP1 in cultured cells. FIG. 6 A illustrates the effect of 1H4 on PP1co-immunoprecipitation with Tat. 293T cells were transfected with Flag-tagged Tat and PP1α-EGFP. FIG. 6 B illustrates that 1H4 has no effect on PP1 association with NIPP1 and PNUTS.

FIG. 7 illustrates the effect of 1H4 compound on a cell proteome.

FIGS. 8 A through F illustrate 1H4 compound disrupts the Tat-mediated translocation of PP1 into the nucleus.

FIG. 9 illustrates chemical structures of PP1-targeting small molecules.

FIG. 10 illustrates a schematic of the experimental approach to developing PP1-targeted, small-molecule inhibitors of filoviruses.

FIG. 11 includes microscopy images of Vero-E6 cells on day 5 post infection with EBOV-eGFP at MOI 0.001 PFU/cell and a single addition of 1E7-03 at 3 μM at 30 min prior the infection (right side): bright field (top) and UV (bottom) microscopy.

FIG. 12 includes UV microscopy images of Vero-E6 cells on various days post infection with EBOV-eGFP at MOI 0.01 PFU/cell and daily addition of 1E7-03 at the indicated concentrations UV microscopy.

FIG. 13 illustrates the multi-step growth kinetics of EBOV-eGFP in Vero-E6 cells, MOI 0.01 PFU/cell and a single addition of 1E7-03 at the indicated time post infection. For the samples in which no virus was detected, the values two-fold below the limit of detection were assigned. Mean EBOV-eGFP concentrations±SE in the medium are indicated.

FIG. 14 is a graph illustrating the effect of time of addition on suppression of EBOV replication by 1E7-03. A multi-step growth kinetics of EBOV-eGFP in Vero-E6 cells, MOI 0.01 PFU/cell and a single addition of 1E7-03 at the indicated time relative the infection. Mean EBOV-eGFP concentrations±SE in the medium are indicated.

FIG. 15 is a graph illustrating the stability of 1E7-03 in water solution. Freshly dissolved 1E7-03 at 1 μM concentration was aliquoted in 50 μL samples. Each sample was incubated at 37° C. for the indicated time and then frozen until analyzed. The samples were analyzed by Electra Spray Mass Spectroscopy (ESI-MS) and amplitude of peak m/z=504.2123 Da, z=1 was recorded. Results show the compound stability during observation time.

FIG. 16 includes graphs illustrating the effect of adding the 1E7-03 compound at 1 μM or 3 μM every 24 hours starting at the indicated time. Mean EBOV-eGFP concentrations±SE in the medium are indicated.

FIG. 17 illustrates the induction of VP30 phosphorylation 293T cells expressing VP30 treated by okadaic acid (OA), 1E7-03 (1E7) or F3 compounds (A) or co-transfected with WT cdNIPP1 or mutant cdNIPP1 (B). VP30 phosphorylation was increased in the presence of 1E7-03 compound and also when cdNIPP1 was co-expressed, as compared to the untreated control (A) or mutant cdNIPP1 (B).

FIG. 18 illustrates optimization of the 1H4 compound.

FIG. 19 illustrates inhibition of EBOV transcription by 1E7-03.

FIG. 20 illustrates the effect of 1E7-03 on VP30 phosphorylation and cellular distribution of PP1.

DETAILED DESCRIPTION

It has been found that certain compounds are suitable for treatment and/or prevention of HIV-1 infections as described in U.S. Pat. No. 8,278,326 to Nekhai et al, which is hereby incorporated by reference. It was surprisingly found that EBOV replication is inhibited with the same and/or similar compounds as those described in U.S. Pat. No. 8,278,326 to Nekhi et al. for the inhibition of HIV-1 virus replication.

As used herein, the terms "alkyl," "alkenyl," and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein. For example, a group containing up to ten carbon atoms is expressed as "1-10 C," "C1-C10" or "C1-10." When heteroatoms (N, O and S typically) are substituted for carbon atoms, such as in heteroalkyl groups, the numbers describing the group (e.g., C1-C6) represent the sum of the number of carbon atoms in the group plus the number of such heteroatoms that are substituted for carbon atoms in the ring or chain being described.

Typically, the alkyl, alkenyl and alkynyl substituents of the compounds described herein are 1-10 C(alkyl) or 2-10 C (alkenyl or alkynyl), preferably 1-8 C (alkyl) or 2-8 C (alkenyl or alkynyl), and in some aspects 1-4 C (alkyl) or 2-4 C (alkenyl or alkynyl). A single group can include more than one type of multiple bond or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. 'Aryl' can include aromatic ring systems containing only carbon as well as aromatic ring systems containing one or more heteroatoms (O, N or S) as ring members. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any mono cyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenyl ethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)- and —$C(Me)_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R7 is alkyl, this alkyl may optionally be substituted by the remaining substituents listed as embodiments for R7 where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example. In some embodiments, where no number of substituents is specified, the number is preferably 0-2.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

"Halo," as used herein includes fluoro, chloro, bromo and iodo. Fluoro and chloro are often preferred.

"Haloalkyl" as used herein includes alkyl groups having one or more halogen substituents. Examples include trifluoromethyl, 2,2,2-trifluoroethyl, 2-chloroethyl, 2-fluoroethyl, and the like.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Where isomers are possible, the invention includes each individual isomer as well as mixtures of isomers. Where a chiral center is present, the invention includes each individual enantiomer at the chiral center as well as mixtures of enantiomers, including racemic mixtures.

In one aspect, the invention provides compounds that inhibit PP1. In some embodiments, the compounds are of formula (I):

(I)

wherein n is 1 or 2;
Ar is phenyl or thienyl, and is optionally substituted;
each $R^1$ is independently $R^6$, $C(O)R^6$, $C(O)$—$OR^6$, or $C(O)N(R^6)_2$;
$R^2$ is H or optionally substituted C1-C6 alkyl, or a group of formula —$C(O)NH$—$R^1$;
$R^3$ is independently at each occurrence selected from halo, $NO_2$, CN, R, OR, $NR_2$;
$S(O)_qR$, COOR, and $CONR_2$, where each R is independently H, C1-C4 alkyl, or C1-C4 haloalkyl;
m is 0-4;
$R^4$ is $R^6$, halo, =O, $COOR^6$, $CON(R^6)_2$, $S(O)_qR^6$, $N(R^6)_2$, or $OR^6$;
p is 0-2;
each q is independently 0-2;
Z is O or $NR^5$;
$R^5$ is $R^6$ or $C(O)R^6$; and
$R^6$ is independently at each occurrence selected from H, C1-C6 alkyl, C5-C6 aryl, and (C5-C6-aryl)-C1-C6 alkyl, where each alkyl and aryl is optionally substituted; provided that n is 2 when Z is O and Ar represents para-halophenyl;
or a pharmaceutically acceptable salt thereof.

In some embodiments, Z is $NR^5$. In such embodiments, $R^5$ is selected from H and —C(O)R', where R' is a C1-C4 alkyl or C1-C4 haloalkyl. In other embodiments, Z is O or NH; preferably Z is O.

In some embodiments, Ar is phenyl, which is optionally substituted. Preferably, wherein n is 1, Ar is not 4-halophenyl.

In other embodiments, Ar is thienyl, which can be substituted. Thienyl can be attached at either position 2 or position 3 of the thiophene ring. In some embodiments, Ar is 2-thienyl, and is optionally substituted. In other embodiments, Ar is optionally substituted 3-thienyl.

In some embodiments, n is 1. In some embodiments, n is 2.

In some embodiments, $R^2$ is H or C1-C4 alkyl or C1-C4 haloalkyl. Preferably, $R^2$ is H, methyl or ethyl.

In some embodiments, m is 0. In other embodiments, m is 1-2.

In some embodiments, when m is not 0, at least one $R^3$ is halo, Cl—C4 alkyl, or C1-C4 haloalkyl.

In some embodiments, p is 0. In other embodiments, p is 1-2.

Where p is not 0, in some embodiments at least one $R^4$ is =O, C1-C4 alkyl, or C1-C4 haloalkyl.

In some embodiments, $R^1$ is an optionally substituted C1-C6 alkyl. In other embodiments, $R^1$ is $C(O)R^6$. In other embodiments, $R^1$ is $C(O)NHR^6$.

The compounds of formula (I) readily form acid addition salts. In some embodiments, the compound of formula (I) is an acid addition salt. In many embodiments, the acid addition salt is a pharmaceutically acceptable salt.

Some specific compounds that have been shown to inhibit Ebola transcription with an effective concentration (IC-50) of about 10 micromolar or less include:

A

B

C
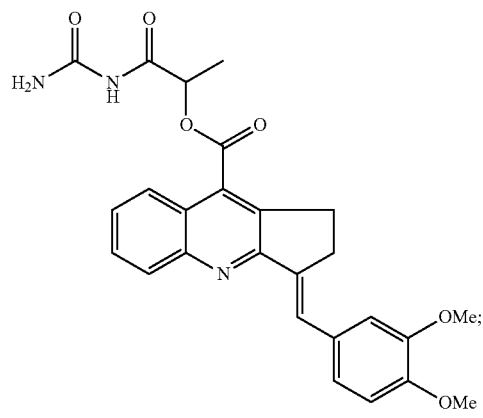
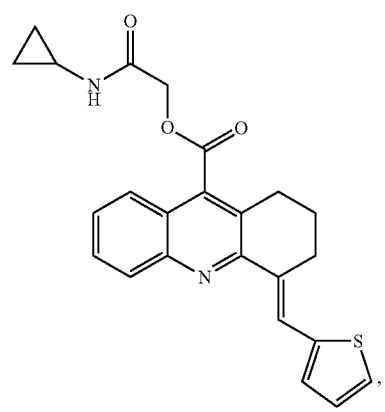
E
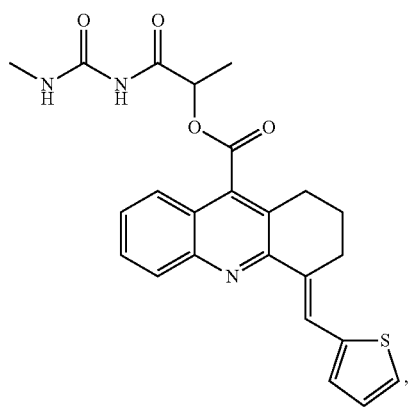
Compound 1H4
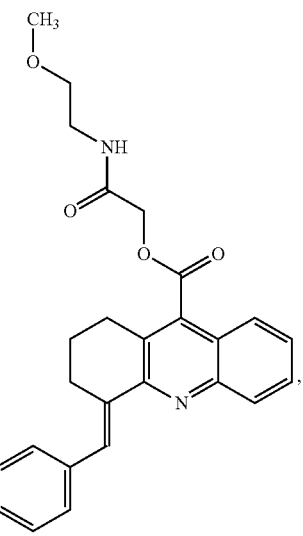
Compound 1G3
Compound 1C7
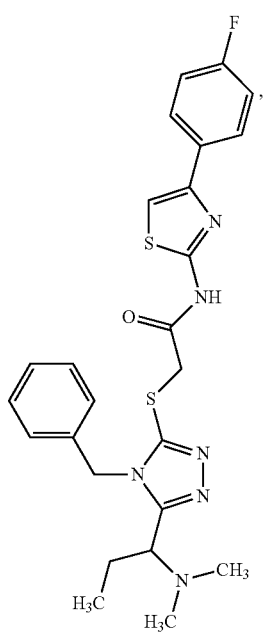

Compound 3C8
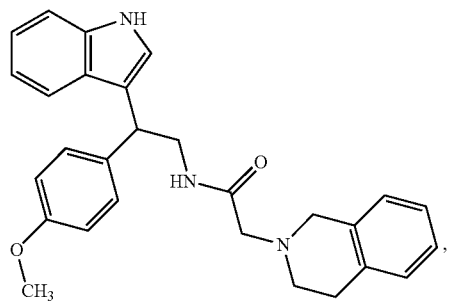
Additional compounds include the following:
1E7
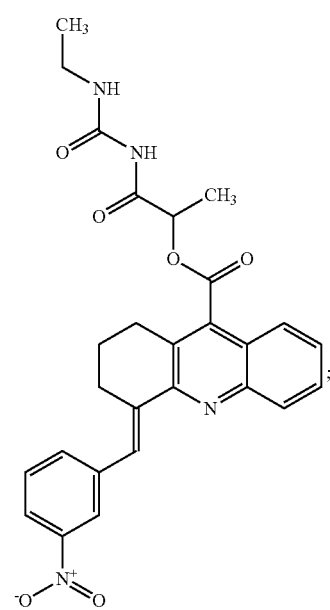
1E7-01
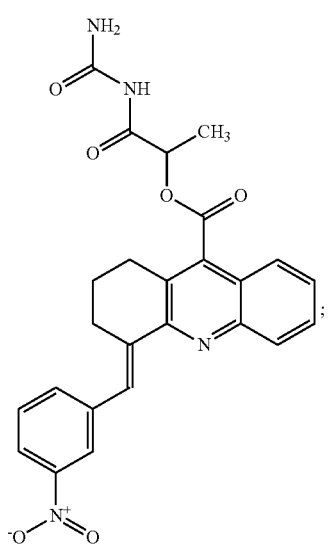
1E7-02
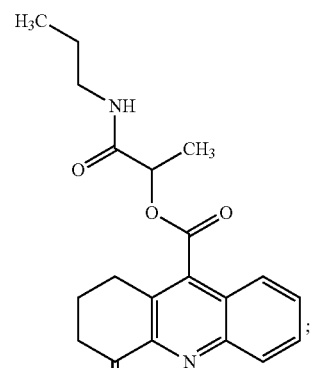
1E7-03
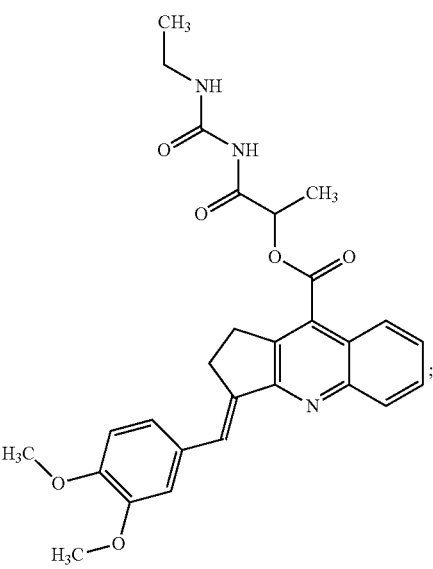
1E7-04
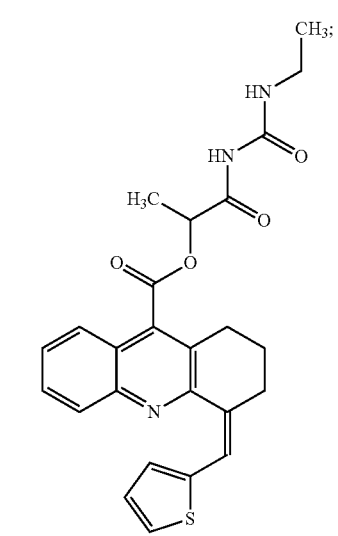

-continued
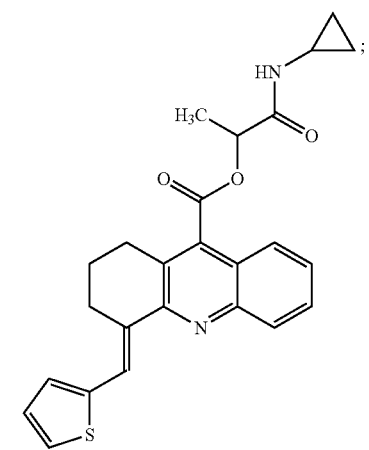
1E7-05
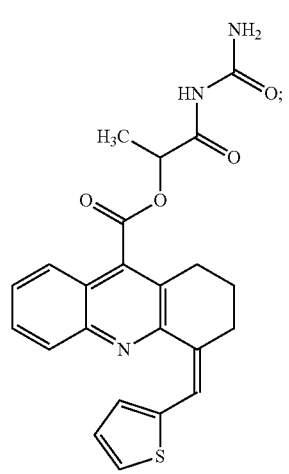
1E7-06
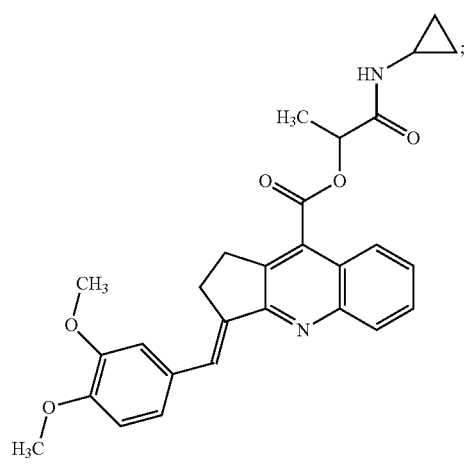
1E7-07
-continued
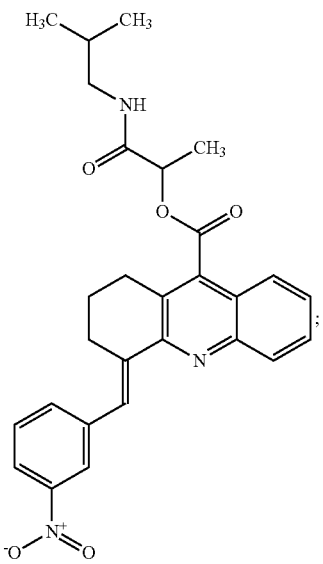
1E7-08
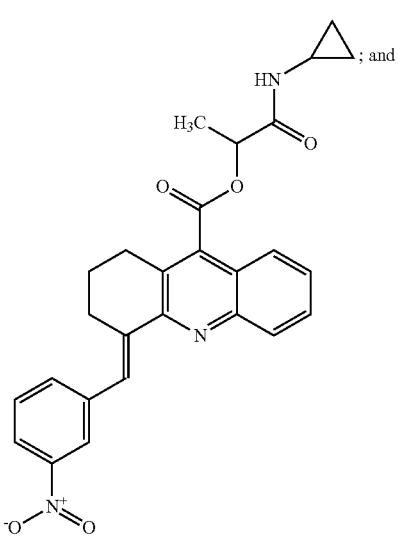
1E7-09
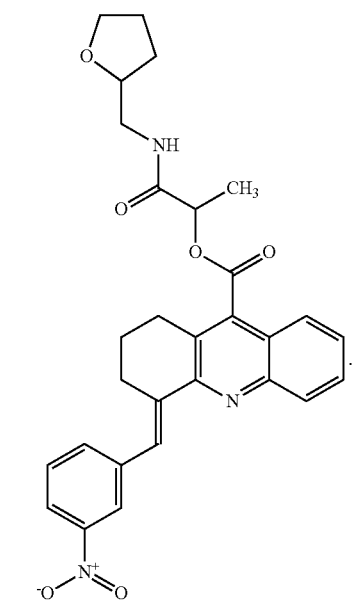
1E7-10

Specific compounds which have been found to treat, inhibit and/or prevent HIV infection and inhibit replication and/or transcription of HIV virus by contacting them with the HIV virus or a cell containing the HIV virus include
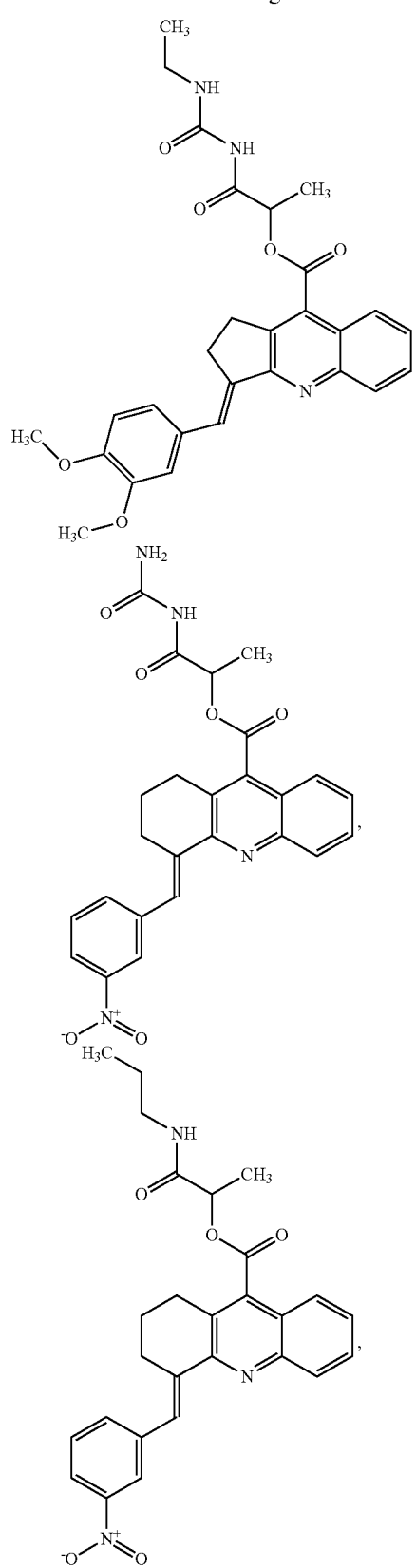
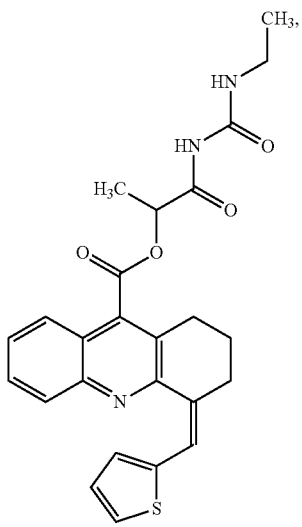
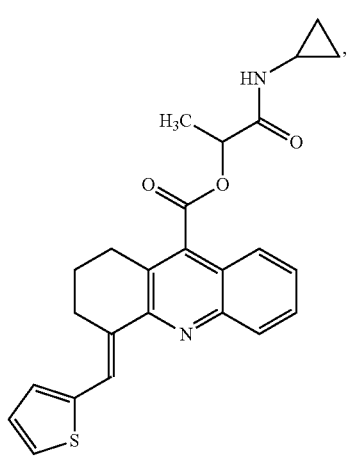
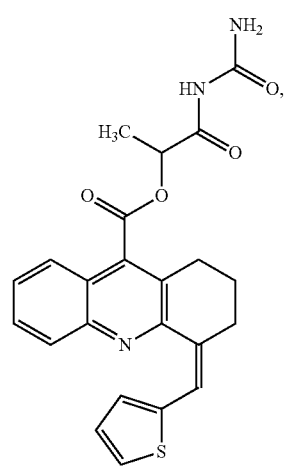

-continued

1E7-07
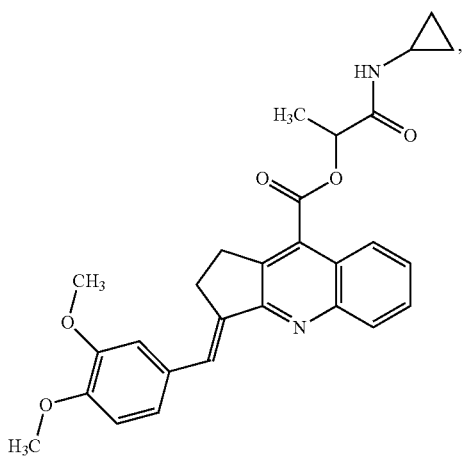

1E7-08
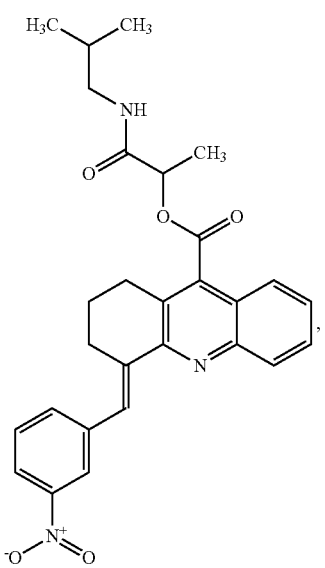

1E7-09
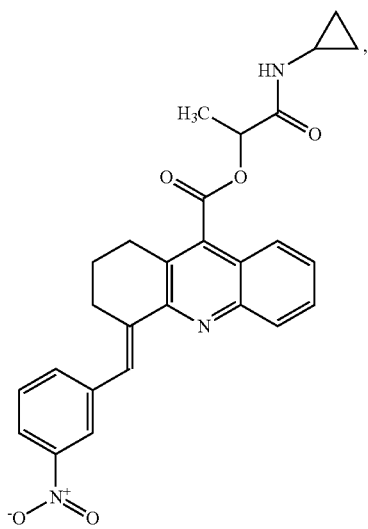

-continued

1E7-10
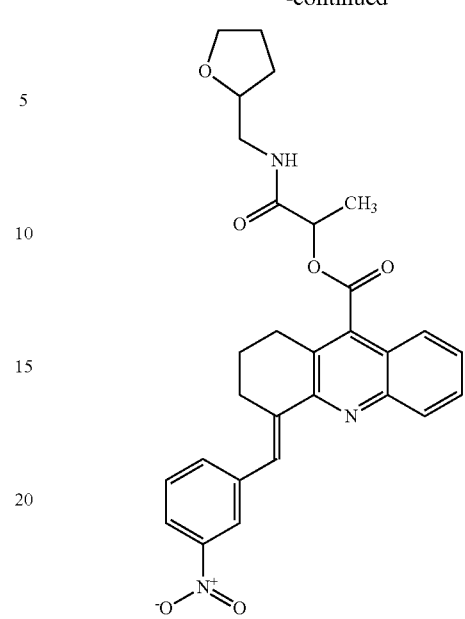

and pharmaceutically acceptable salts of these compounds.

The compounds described herein can be prepared using well-known reactions, starting from available starting materials such as 1,2,3,4-tetrahydroacridine-9-carboxylic acid as summarized in Scheme 1. This acid can readily be converted to an ester or an amide to provide compounds wherein Z is O or N, respectively, using standard conditions that are well known in the art. The wide array of available alcohols and amines enables one to synthesize many compounds with various $R^1$ and $R^2$ groups incorporated therein. Once an ester or amide is formed from the carboxylate, the intermediate ester or amide can be condensed with various available aldehydes to introduce the "Ar—CH=" group on the saturated ring, using a base such as potassium tert-butoxide in a polar, aprotic solvent such as DMSO, DMF, DME, or THF, or in a non-nucleophilic protic solvent such as t-butanol. It is also possible to form a hindered ester of the starting carboxylic acid, such as a t-butyl ester, and condense the acridine ester with an aldehyde as described, then hydrolyze the ester to make an intermediate carboxylic acid compound having the Ar—CH= group in place. This intermediate can then be coupled to various available or readily accessible alcohols or amines to produce the products of formula (I). Methods for such coupling reactions are well known in the art.

Scheme 1: Synthesis of compounds of Formula (I).

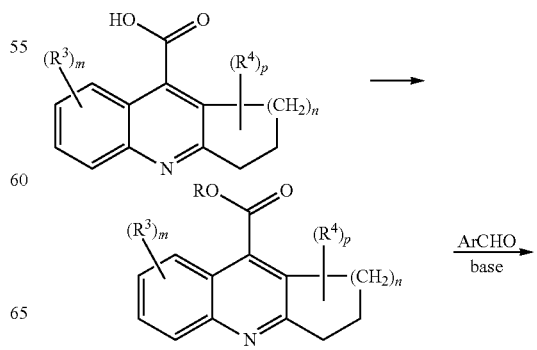

-continued

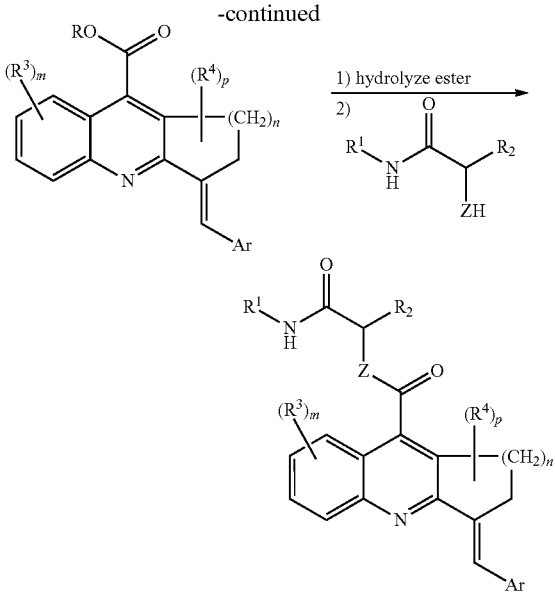

The compounds described herein are shown to be effective inhibitors of replication of Ebola in cell lines. Accordingly, the compounds are useful to treat, inhibit and/or prevent Ebola infections in animals, including humans. Use of the compounds includes administering to a subject in need thereof an effective amount of a compound of formula I or other compounds described herein or pharmaceutical compositions thereof. Pharmaceutical compositions comprising an effective amount of at least one compound of formula I or other compounds described herein are provided and include at least one compound of formula I or other compounds described herein admixed with at least one pharmaceutically acceptable excipient. In some embodiments, the method includes identifying a subject in need of such treatment. The compounds described herein may be used for the manufacture of a medicament and for the manufacture of a medicament for the treatment of Ebola infection.

The compounds of formula I and other compounds described herein may be administered by oral, parenteral (e.g., intramuscular, intraperitoneal, intravenous, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. Methods and formulations for each of these routes of administration are within the knowledge and expertise of a person of ordinary skill in the art.

It is also contemplated that the compounds of the present invention may be used in combinations with one or more agents useful in the prevention or treatment of Ebola. Examples of such agents include: (1) small molecule inhibitors of EBOV entry, heat shock protein 90, virus-cell fusion, and the endosomal membrane protein Niemann-Pick C1, each of which had only a modest anti-viral effect.

The compounds of formula I and other compounds described herein may be used to treat animals, including but not limited to, mice, rats, guinea pigs and primates, including humans.

The compounds of formula I and other compounds described herein may form hydrates or solvates, which are included in the scope of the claims. When the compounds of formula I and other compounds described herein exist as regioisomers, configurational isomers, conformers, or diasteroisomeric forms, all such forms and various mixtures thereof are included in the generic formulas. It is possible to isolate individual isomers using known separation and purification methods, if desired. For example, when a compound of formula I is a racemate, the racemate can be separated into the (S)-compound and (R)-compound by optical resolution. Individual optical isomers and mixtures thereof are included in the scope of the generic formula.

The compounds of the invention can be used in their neutral form or as a salt. The compounds of Formula I and other compounds described herein readily form acid addition salts, and in some embodiments, the acid addition salts are preferable for use in the methods and pharmaceutical compositions of the invention. Formation of such salts is within the ordinary level of skill in the art and can be achieved by contacting a compound of Formula I or other compounds described herein with a suitable acid. The salt used can be any stable salt; in some embodiments, the acid is selected to provide a pharmaceutically acceptable salt. Examples of pharmaceutically acceptable salts are organic acid addition salts formed with acids that form a physiological acceptable anion, for example, tosylate, methanesulfonate, besylate, acetate, formate, citrate, malonate, tartrate, succinate, benzoate, ascorbate, a-ketoglutarate, lactate, and a-glycerophosphate. Suitable inorganic salts may also be formed, including hydrochloride, sulfate, bisulfate, phosphate, nitrate, hydrobromide, and the like.

Compositions are provided that include a pharmaceutically acceptable carrier or diluent and an effective amount of a compound of Formula I or other compounds described herein. The pharmaceutical compositions preferably comprise at least one acceptable diluent or excipient other than water, methanol, ethanol, or DMSO. In some embodiments, the pharmaceutical composition comprises at least one excipient selected from a buffer, saline, and a mono- or di-saccharide.

A compound of formula I and other compounds described herein may be administered alone or as an admixture with a pharmaceutically acceptable carrier (e.g., solid formulations such as tablets, capsules, granules, powders, etc.; liquid formulations such as syrups, injections, etc.) and may be orally or non-orally administered. Examples of non-oral formulations include injections, drops, suppositories, and pessaries.

In the treatment or prevention of conditions in a human subject, an appropriate dosage level will generally be about 0.01 to 500 mg per kg patient body weight per day which can be administered in singe or multiple doses. Preferably, it is believed the dosage level will be about 0.1 to about 100, or from about 0.1 to about 10 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703,055 (Felgner, et al.) and Gregoriadis, Liposome Technology vols. I to II (2nd ed. 1993).

The pharmaceutical dosage forms suitable for injection or infusion can include sterile aqueous solutions or dispersions or sterile powders comprising the active ingredient that-are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortman (U.S. Pat. No. 4,820,508).

Compounds may be formulated with a solid carrier, which can include finely divided solids such as talc, clay, microcrystalline cellulose, silica, or alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. It is believed the concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carriers) and/or excipient(s) in liquid form or finely divided solid form, or both, and then shaping the product if required. The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

Methods for assessing the activity of compounds of the invention against Ebola transcription are well known in the art and were used to test compounds of the invention for activity.

The following examples describe various aspects of the application. These examples should not be interpreted as limiting the scope of the present application as described in the accompanying claims. Unless otherwise specified all parts and percentages are by weight and reported measurements and other data were obtained under ambient conditions.

Examples

EBOV and MARV belong to the order Mononegavirales (non-segmented, negative-strand RNA viruses), which comprises a large number of biologically diverse viruses. All of them have an RNA-dependent RNA polymerase complex consisting of three proteins: nucleoprotein (N), phosphoprotein (P), and the large subunit of polymerase (L), which mediates both replication and transcription of the viral genome. The EBOV and MARV polymerases include the three proteins NP (nucleoprotein), VP35 (phosphoprotein), and L (polymerase). In addition, filovirus polymerases also include the VP30 protein, which is a transcription elongation factor unique to these viruses; respiratory syncytial virus (RSV) is the only other non-segmented, negative-strand virus, known to have a protein with a similar function (M2-1) (Collins, P. L., et al., *Production of infectious human respiratory syncytial virus from cloned Cdna confirms an essential role for the transcription elongation factor from the 5' proximal open reading frame of the M2 Mrna in gene expression and provides a capability for vaccine development*. Proc Natl Acad Sci USA, 1995. 92(25): p. 11563-7). It should be noted that while EBOV VP30 was demonstrated to be critically important for transcription, no similar function of MARV was initially established in the mini-genome system (Muhlberger, E., et al., *Comparison of the transcription and replication strategies of marburg virus and Ebola virus by using artificial replication systems*. J Virol, 1999. 73(3): p. 2333-42). However, the supportive effect of VP30 on MARV transcription and replication was established in a recently published infectious virus-like particle assay (Wenigenrath, J., et al., *Establishment and application of an infectious virus-like particle system for Marburg virus*. The Journal of general virology, 2010. 91(Pt 5): p. 1325-34). The VP30 protein of EBOV binds to the leader region of the viral genomic RNA through the amino acid residues 26 to 40, which are rich in arginines (John, S. P., et al., *Ebola Virus VP30 Is an RNA Binding Protein*. J Virol, 2007. 81(17): p. 8967-76). In addition, EBOV VP30 protein is phosphorylated within two serine clusters at positions 29-31 and 42-46 and on threonine at position 52, located close to the RNA-binding domain (Modrof, J., et al., *Phosphorylation of VP30 impairs ebola virus transcription*. J Biol Chem, 2002. 277 (36): p. 33099-104). MARV VP30 is phosphorylated on serine 40-51 residues (Modrof, J., et al., *Phosphorylation of Marburg virus VP30 at serines 40 and 42 is critical for its interaction with NP inclusions*. Virology, 2001. 287(1): p. 171-82). Phosphorylation of EBOV VP30 blocks the ability of the viral polymerase to function in the transcription mode (Martinez, M. J., et al., *Role of Ebola virus VP30 in transcription reinitiation*. J Virol, 2008. 82(24): p. 12569-73), likely due to the inability to bind RNA. Phosphorylated EBOV VP30 is dephosphorylated in vitro by protein phosphatase 1 (PP1). Inhibition of PP1 by okadaic acid also inhibited transcription activation by VP30, similarly to the inhibition of HIV-1 transcription by okadaic acid or PP1 inhibitors (Ammosova, T., et al., *Dephosphorylation of CDK9 by protein phosphatase 2A and protein phosphatase-1 in Tat-activated HIV-1 transcription*. Retrovirology, 2005. 2(1): p. 47). Thus, filovirus transcription and replication are critically dependent on VP30 dephosphorylation by PP1, which can be targeted to inhibit EBOV. Comparison of the VP30 proteins from EBOV Zaire, Sudan, Bundibugyo and Ivory Coast, and MARV showed a remarkable similarity of the phosphorylation sites at the N-termini of the VP30 proteins for these filoviruses (FIG. 1). This similarity suggested the likelihood of developing a panfilovirus drug that targets PP1.

Example 1

Targeting PP1 for the Inhibition of HIV-1 Transcription

HIV-1 transcription is activated by the HIV-1 Tat protein that recruits CDK9/cyclin T1 to HIV-1 TAR RNA (FIG. 2) (Nekhai, S., and K.-T. Jeang, *Transcriptional and posttranscriptional regulation of gene expression: role of cellular factor*. Future Microbiology, 2006. 4:417-426.). The recruited CDK9 phosphorylates RNA polymerase II carboxyl-terminal domain CTD and promotes transcription elongation of HIV-1 genes (FIG. 2). In earlier studies, HIV-1 transcription was found to be induced by PP1 (Nekhai, S., et al., HIV-1 Tat-associated RNA polymerase C-terminal domain kinase, CDK2, phosphorylates CDK7 and stimulates Tat-mediated transcription. Biochem J, 2002. 364(Pt 3): p. 649-57; Bharucha, D. C., et al., A protein phosphatase from human T cells augments tat transactivation of the human immunodeficiency virus type 1 long-terminal repeat. Virology, 2002. 296(1): p. 6-16). When nuclear inhibitor of PP1 (NIPP1) was expressed in cultured cells, Tat-induced HIV-1 transcription was blocked (Ammosova, T., et al., *Nuclear protein phosphatase-1 regulates HIV-1 transcription*. J Biol Chem, 2003. 278(34): p. 32189-94). A typical PP1-binding regulatory protein contains "RVxF" motif which binds to a pocket on the surface of PP1 (Egloff, M. P., et al., *Structural basis for the recognition of regulatory subunits by the catalytic subunit of protein phosphatase 1*. Embo J, 1997. 16(8): p. 1876-87). Analysis of the sequence of HIV-1 Tat revealed the presence of a $^{35}$QVCF$^{38}$ sequence that closely resembled PP1-binding "RVxF" motif and that directly bound PP1 (Ammosova, T., et al., *Nuclear targeting of protein phosphatase-1 by HIV-1 Tat protein*. J Biol Chem, 2005. 280(43): p. 36364-71). It was shown that the Tat $^{35}$QVCF$^{38}$ sequence interacts with PP1 in vitro, translocates PP1 to the nucleus in cultured cells, and is critical for HIV-1 transcription. It was also shown that dephosphorylation of CDK9 Thr 186 by PP1 dissociates CDK9/cyclin T1 from the inhibitory 7SK RNA (Ammosova, T., et al., *Expression of a protein phosphatase 1 inhibitor, cdNIPP1, increases CDK9 threonine 186 phosphorylation and inhibits HIV-1 transcription*. J Biol Chem, 2011. 286(5): p. 3798-804) and that dephosphorylation of CDK9 Ser 175 by PP1 activates enzymatic activity of CDK9 (Ammosova, T., et al., *Protein phosphatase-1 activates CDK9 by dephosphorylating Ser175*. PLOS One, 2011. 6: p. e18985). Taken together, these results suggest that interaction of HIV-1 Tat protein with PP1 promotes activation of CDK9/cyclin T1 and made it available for subsequent recruitment (FIG. 2). These findings suggested a possibility of identifying small molecules that can disrupt the interaction of Tat and PP1 and inhibit HIV-1 transcription. Thus development was focused on small molecule-mimetics of the RVxF motif to find a novel HIV-1 inhibitor.

Design of Small Molecule "RVxF" Peptide-Mimetics.

The PP1 holoenzyme consists of a constant catalytic subunit (PP1α, PP1β/δ or PP1γ) (here and below PP1 refers to its catalytic subunits) and a variable regulatory subunit (PIP) that determines the localization, activity, and substrate-specificity of the phosphatase (Bollen, M. and M. Beullens, *Signaling by protein phosphatases in the nucleus.* Trends Cell Biol, 2002. 12(3): p. 138-45). The catalytic subunits of PP1 are highly conserved among eukaryotes and adopt the same compact α/β fold and share the same catalytic mechanism (Shi, Y., *Serine/threonine phosphatases: mechanism through structure.* Cell, 2009. 139(3): p. 468-84). PIPs or their PP1-binding domains, that are PP1 unbound, are often lacking three dimensional structure and are highly disordered (Bollen, M., et al., *The extended PP1 toolkit: designed to create specificity.* Trends Biochem Sci, 2010. 35(8): p. 450-8). Upon binding to PP1, PIPs such as DARPP-32, Inhibitor-2 and spinophilin form extensive and unique interaction with PP1. Because of the nearly identical structure of the three constant catalytic subunits and naturally disordered regulatory subunits, it was chosen to target the interaction site on PP1 catalytic, rather than regulatory subunit. Major PP1 regulators, such as NIPP1 bind PP1 with nanomolar affinity to modulate the dephosphorylation of a wide range of PP1 substrates. It was found that Tat binds PP1 in a similar manner to how NIPP1 binds PP1, except that the Tat-PP1 interaction is weaker and occurs with micromolar affinity. Interestingly, a Q35R mutation in Tat conferred a higher Tat-PP1 affinity, but also inactivated Tat, presumably because a tighter PP1-association prevents Tat-binding to CDK9/cyclin T1.

Figure 3:
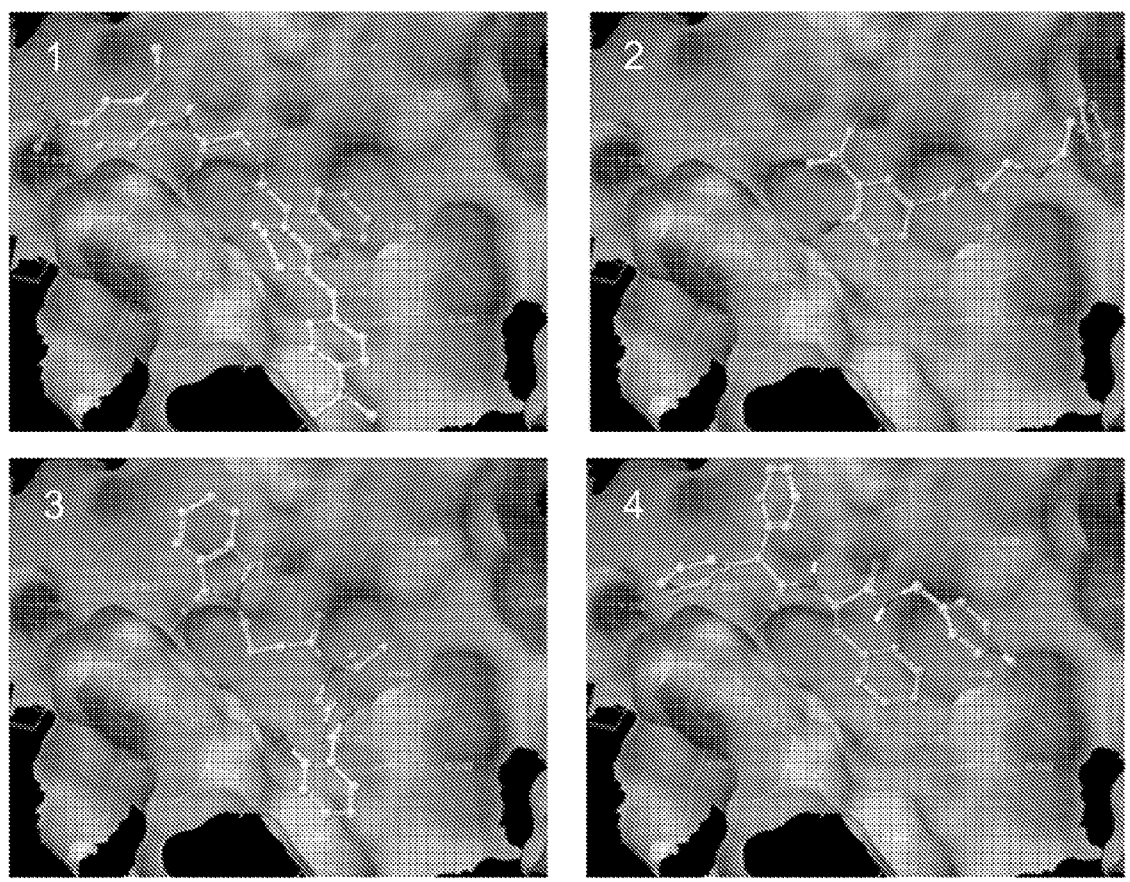

Design and preparation of a library of small molecule compounds that mimic the interaction of the RVxF motif with PP1 was also undertaken. Coordinates from a crystal structure of the complex of PP1γ were used with RRVSFA peptide for docking experiments. Over 300,000 compounds from Enamine (Ukraine) were virtually docked using QXP docking engine. Compounds fell into one of the four binding modes (FIG. 3). In total, 1,572 compounds were further computationally processed using sequential filtering protocols calculated by qxp+(McMartin, C. and R. S. Bohacek, *QXP: powerful, rapid computer algorithms for structure-based drug design.* J Comput Aided Mol Des, 1997. 11(4): p. 333-44) that included pI, an overall estimate of binding potency; Cntc, a description of ligand-protein contacts; Intl, an estimation of the ligand strain; and Hbnd, a description of the hydrogen bond network. Compounds with pI>4, Cntc>55, Intl<8 and Hbnd<−3 were considered for further analysis. These criteria excluded compounds that had poor geometry or strained structures, and yielded 262 compounds that were further evaluated biologically for inhibition of HIV-1 transcription and replication.

Identification of HIV-1 Inhibitory Compounds.

All 262 candidate compounds were evaluated for inhibition of Tat-dependent HIV-1 transcription using a previously described (Nekhai, S., et al., *A novel anticancer agent ARC antagonizes HIV-1 and HCV.* Oncogene, 2007. 26(26): p. 3899-903) reporter assay. CEM-GFP cells were infected with an adenovirus expressing HIV-1 Tat activator protein, and activation of the LTR-GFP reporter by Tat in CEM cells produced heightened GFP fluorescence. Infected CEM-GFP cells were incubated with 25 μM of each compound for 48 hours. The cytotoxicity was evaluated by staining cells with propidium iodide and measuring red fluorescence. Sixty compounds that inhibited HIV-1 transcription by at least 80% at 25 μM were selected and further analyzed at different concentrations to determine the 50% inhibitory concentration ($IC_{50}$) for the inhibition of transcription. This dose-dependent analysis identified 17 compounds that inhibited HIV-1 transcription in CEM-GFP cells with $IC_{50}$ below 25 μM, and 6 compounds that inhibited HIV-1 transcription at $IC_{50}$ below 15 μM (Table 1). Amongst the latter 6, only one compound, 1H4, was not cytotoxic at the concentrations tested.

TABLE 1

Selected compounds that inhibited HIV-1 transcription.

| Structure | ID | Inhibition of HIV-1 Transcription in CEM-GFP cells ($IC_{50}$, μM) | Toxicity in CEM cells, ($IC_{50}$, μM) |
| --- | --- | --- | --- |
| [structure] | T0516-8237 (1H4) | 12.5 | >25 |
| [structure] | T5251659 | 10 | 6 |

TABLE 1-continued

Selected compounds that inhibited HIV-1 transcription.

| Structure | ID | Inhibition of HIV-1 Transcription in CEM-GFP cells (IC$_{50}$, μM) | Toxicity in CEM cells, (IC$_{50}$, μM) |
|---|---|---|---|
| 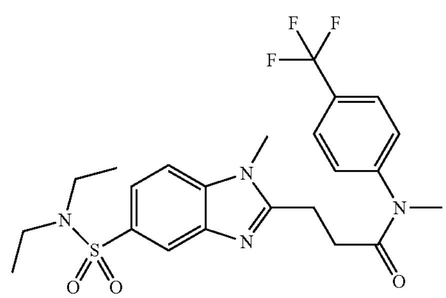 [SMILES: CCN(CC)S(=O)(=O)c1ccc2c(c1)nc(CCC(=O)N(C)c1ccc(C(F)(F)F)cc1)n2C] | T5326526 | 15 | 10 |
| 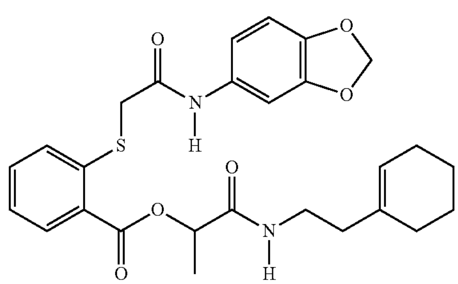 [SMILES: CC(OC(=O)c1ccccc1SCC(=O)Nc1ccc2c(c1)OCO2)C(=O)NCCC1=CCCCC1] | T5369370 | 10 | 15 |
| 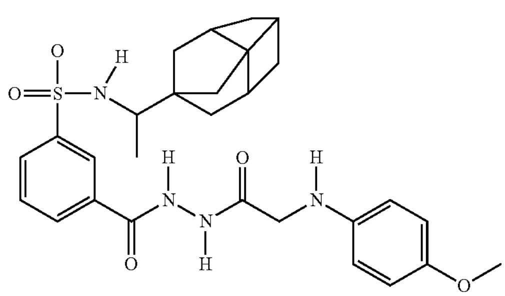 | T5420253 | 15 | 15 |
| 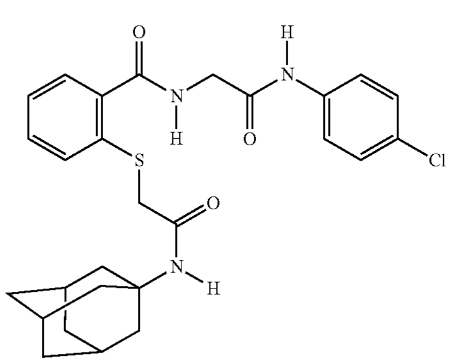 [SMILES: O=C(CNC(=O)c1ccccc1SCC(=O)NC12CC3CC(CC(C3)C1)C2)Nc1ccc(Cl)cc1] | T5498680 | 5 | 5 |

TABLE 1-continued

Selected compounds that inhibited HIV-1 transcription.

| Structure | ID | Inhibition of HIV-1 Transcription in CEM-GFP cells (IC$_{50}$, µM) | Toxicity in CEM cells, (IC$_{50}$, µM) |
|---|---|---|---|
| [structure] | T5481237 | 15 | 20 |
| [structure] | T5551920 | 15 | 15 |

1H4 Inhibited the Interaction of Tat with PP1 In Vitro.

Figure 4:
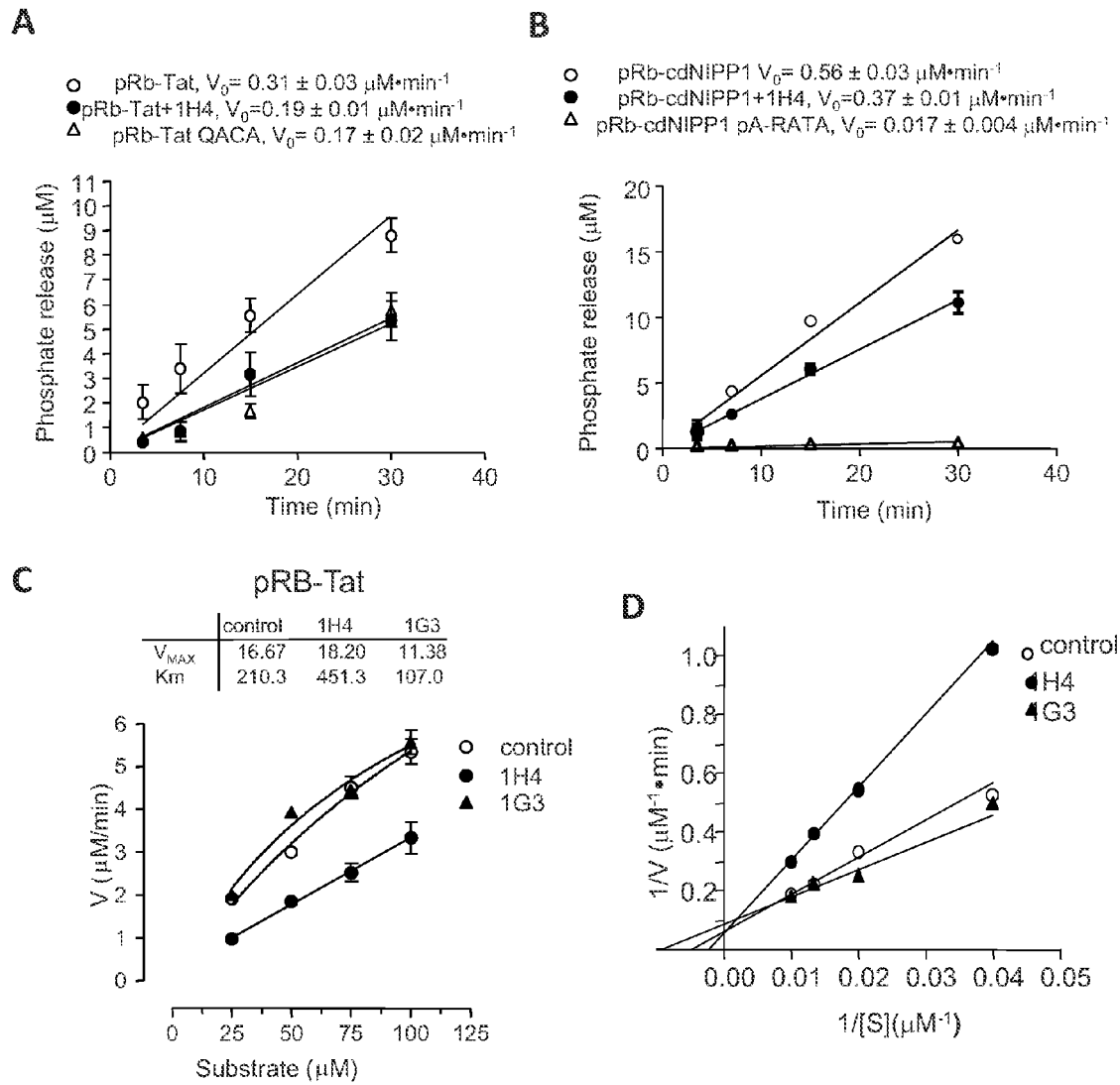

Analysis of the effect of 1H4 on the binding of the Tat RVxF sequence to PP1 using hybrid PP1 substrates containing a substrate phosphopeptide linked to RVxF-containing sequences derived from Tat or NIPP1 was undertaken. As the substrate phosphopeptide, a retinoblastoma protein-derived HIPR(pS)PYKFPSSPLR (SEQ ID NO: 1) peptide (pRb) was used that is efficiently dephosphorylated by PP1 but not by the enzymatically-related PP2A (Ammosova, T., et al., Protein Phosphatase-1 Activates CDK9 by Dephosphorylating Ser175. PLOS One, 2011. 6(4): p. e18985). The pRb peptide was linked to an extended RVxF-containing sequence derived from Tat (KKCCFHCQVCFITK, SEQ ID NO: 2) (pRb-Tat peptide) or the central domain of NIPP1 (KRKRKNSRVTFSED, SEQ ID NO: 3). Recombinant PP1α was assayed with pRb-Tat (WT or QACA mutant, 120 µM) in the absence or presence of 1H4 as indicated. The reactions were stopped at indicated time points and the phosphate release was quantified by malachite green assay. Initial velocity was calculated by linear regression in Prism. Recombinant PP1α was assayed with pRb-cdNIPP1 in the absence or presence of 1H4 as indicated. Mutant pRb cdNIPP1 pA-RATA was used as negative control. The reactions were stopped at indicated time points and the phosphate release was quantified by malachite green assay. Initial velocity was calculated by linear regression in Prism. The pRb-Tat peptide was efficiently dephosphorylated by PP1 in vitro (FIG. 4A, V$_0$=0.31 µM·min$^{-1}$). Similar dephosphorylation kinetics were observed for the pRb-NIPP1 peptide (FIG. 4B, Vo=0.56 µM·min$^{-1}$), but not for the mutant pRb-NIPP1 pA-RATA peptide (HIPR(pS)PYKFPSSPL-RAAAAASRATASED, SEQ ID NO: 4) which was a very poor PP1 substrate (FIG. 4B, Vo=0.004 µM·min$^{-1}$). Interestingly, the dephosphorylation of the pRb peptide (HIPR(pS)PYKFPSSPL, SEQ ID NO: 5) was significantly slower than pRb-Tat or pRb-NIPP1 peptides (Vo=0.014 µM·min$^{-1}$, data not shown). The increased dephosphorylation of pRb-Tat and pRb-NIPP1 peptides suggests that the extended RVxF motif might accelerate the dephosphorylation reaction likely due to the binding to PP1 during the process of substrate recognition. Dephosphorylation of the pRb-Tat QACA peptide (HIPR(pS)PYKFPSSPLR KKCCFHCQA-CAITK, SEQ ID NO: 6) having a mutation in the RVxF sequence was significantly reduced (FIG. 4A, V$_0$=0.17 µM·min$^{-1}$). Addition of 1H4 at 3-fold molar excess (480 µM) over pRb-Tat (160 µM) inhibited pRb-Tat dephosphorylation and reduced the rate of dephosphorylation (FIG. 4A, V$_0$=0.19 µM·min$^{-1}$) to the rate of pRb-Tat QACA dephosphorylation (FIG. 4A, V$_0$=0.17 µM·min$^{-1}$). The addition of 1H4 also reduced the rate of pRb-cdNIPP1 phosphorylation (FIG. 4B, V$_0$=0.37 µM·min$^{-1}$). These observations suggest that 1H4 is likely to interfere with the interaction of the RVxF motif with PP1. To further investigate the effect of 1H4 on the dephosphorylation of the pRb-Tat peptide, the initial velocity versus pRb-Tat peptide substrate concentration plots was analyzed. Initial rates of pRb-Tat peptide dephosphorylation by PP1α were assayed at the indicated concentrations of the substrate in the absence or presence of 300 mM 1H4 or non-HIV-1 inhibitory 1G3. The amount of the released phosphate was quantified with malachite green. The VMAX and Km were calculated by non-linear regression analysis in Prism with the assumption that 25% of the substrate contained the phosphate group. Transformation of the data to Lineweaver-Burk plot (panel E) showed competitive inhibition of pRb-Tat dephosphorylation. Addition of 1H4 inhibited pRb-Tat dephosphorylation by increasing Km but not Vmax (FIG. 4B). In contrast, a non-HIV-1 inhibitory 1G3 compound did not inhibit pRb-Tat dephosphorylation but instead induced dephosphorylation as evidenced by the decreased Km (FIG. 4B). Visualization on a Lineweaver-Burk plot showed a competitive nature of pRb-Tat inhibition by 1H4 (FIG. 4C), which is evidenced by a common intercept on the 1/Vo axis. This was expected because the dephosphorylation site and the RVxF-containing sequence were fused into one hybrid substrate and 1H4 interferes with the binding of this substrate to PP1. Taken together, these results demonstrate that 1H4 interferes with the binding of the RVxF motif to PP1.

1H4 does not Inhibit Enzymatic Activity of PP1 In Vitro.

Figure 5:
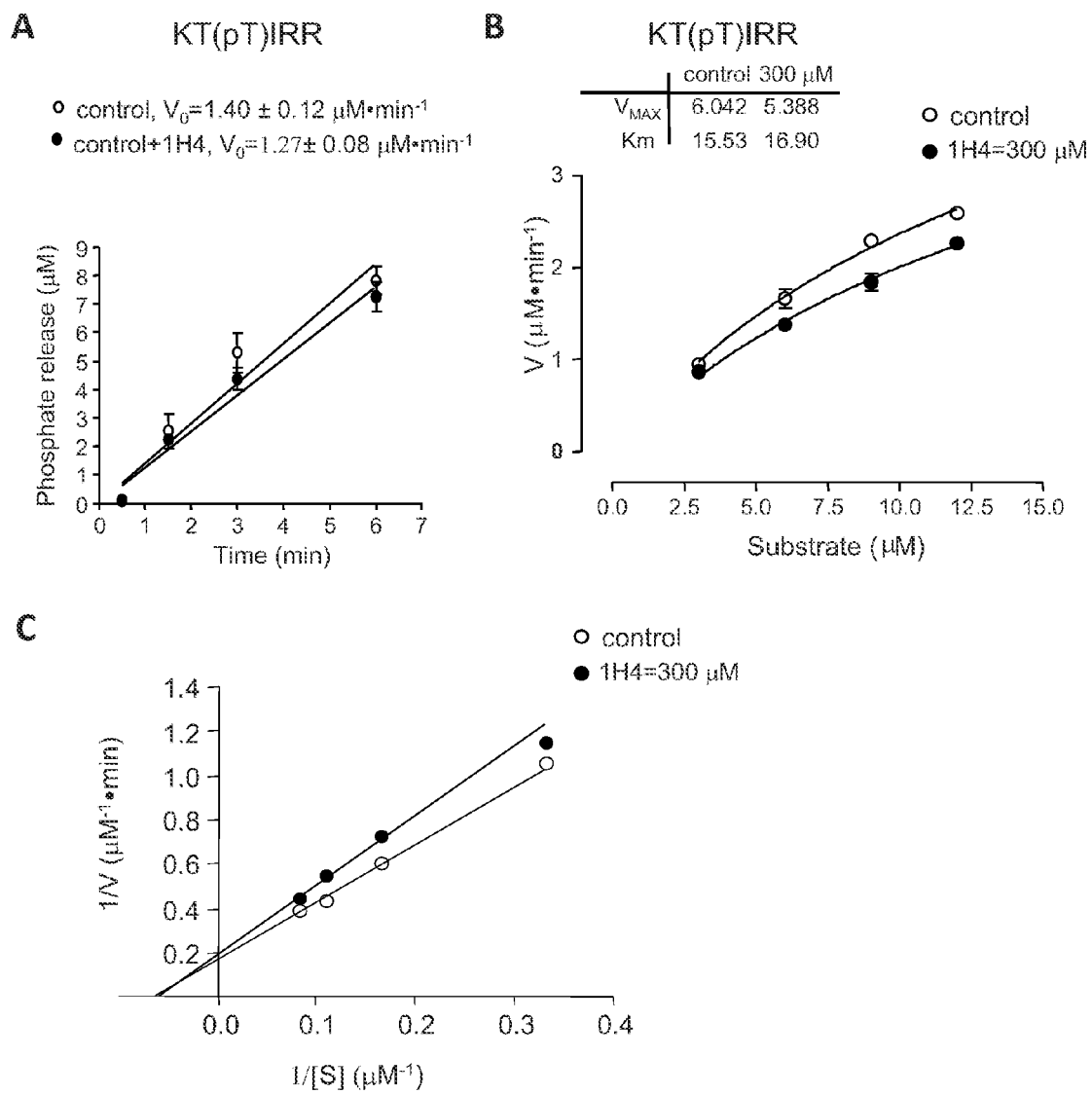

To determine whether 1H4 has an effect on the enzymatic activity of PP1, recombinant PP1α and a generic substrate, phosphorylated KT(pT)IRR (SEQ ID NO: 7) peptide which is recognized equally well by PP1 and PP2A was used. Recombinant PP1α (0.005 Units) was assayed with KT(pT)IRR (SEQ ID NO: 7) peptide (3 mM) in the absence or presence of 1H4, and the reaction was stopped at indicated time points by the addition of malachite green solution. The amount of released phosphate was quantified by the absorbance and phosphate concentration was recalculated using standards. Initial velocity was calculated by linear regression in Prism. The KT(pT)IRR (SEQ ID NO: 7) peptide (3 μM) was efficiently dephosphorylated by PP1α (FIG. 5A, $V_0=1.4$ μM·min$^{-1}$). Very little inhibition of PP1α activity was observed when 1H4 (300 μM) was added to the reaction (FIG. 5A, $V_0=1.3$ μM·min$^{-1}$). Initial rates of KT(pT)IRR (SEQ ID NO: 7) peptide dephosphorylation by PP1α were assayed at the indicated concentrations of the substrate in the absence or presence of 300 mM 1H4. The amount of released phosphate was quantified with malachite green. The VMAX and Km were calculated by non-linear regression analysis for Michaelis-Menten equation in Prism. The data were transformed to Lineweaver-Burk representation shown in panel C. The effect of 1H4 on PP1 enzymatic activity was investigated by analyzing the initial velocity versus KT(pT)IRR (SEQ ID NO: 7) peptide substrate concentration plots in the absence and presence of 1H4 that were approximated by Michaelis-Menten equation (FIG. 5B) and also visualized in Lineweaver-Burk representation (FIG. 5C). The addition of 1H4 had minimal effect on Vmax and Km (FIG. 5B) further supporting the conclusion that 1H4 has no direct effect on PP1 enzymatic activity.

1H4 Prevents the Intracellular Interaction of Tat with PP1.

Figure 6:
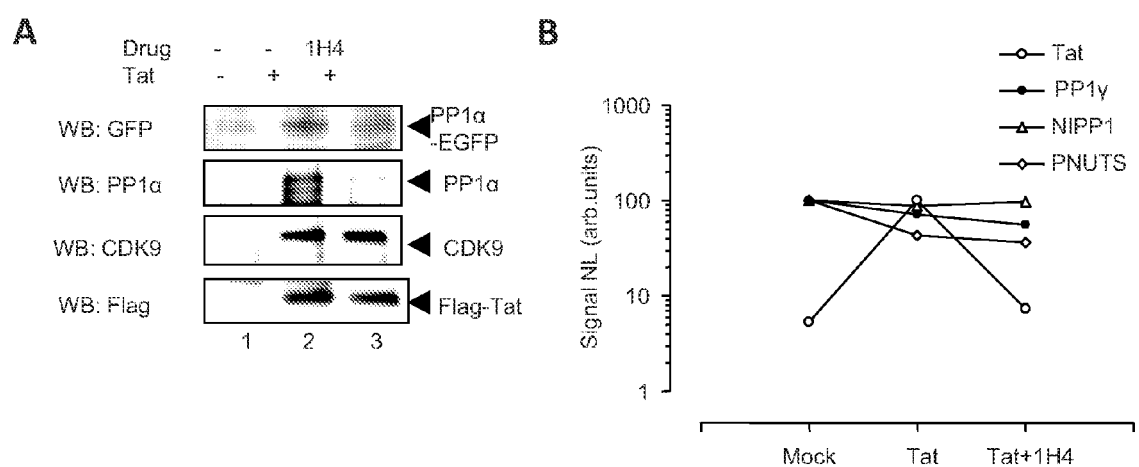

During HIV-1 infection, Tat facilitates PP1α translocation into the nucleus. To analyze whether 1H4 disrupts the interaction of Tat with PP1α, PP1α-EGFP was expressed along with Flag-Tat, in the absence and presence of 1H4 (FIG. 6A). Flag-Tat co-precipitated with PP1α-EGFP (FIG. 6A, IP: α-Flag, lane 2). Flag-Tat was immunoprecipitated with anti-Flag antibodies from the cells extracts and probed with antibodies against EGFP to detect PP1 and a-Flag to detect Tat. Lane 1, untreated whole cell extract; lane 2, cells treated with 10 mM 1H4; lane 3, mock-transfected cells. The addition of 10 μM 1H4 reduced the amount of PP1α-EGFP that co-precipitated with Tat (FIG. 6A, lane 3). Similarly, 1H4 reduced the association of Tat with endogenous PP1α as detected with PP1α-specific antibodies (FIG. 6A second panel, lanes 2 and 3). In contrast, 1H4 had no effect on the association of Tat with CDK9/cyclin T1 as shown by the equal presence of CDK9 (FIG. 6A, third panel lanes 2 and 3). Thus, 1H4 appears to interrupt the interaction between Tat and PP1α, without affecting the association of Tat with CDK9 thereby decreasing the amount of PP1 available to regulate HIV-1 transcription.

1H4 has No Effect on the Interaction of PP1 with NIPP1 and PNUTS.

To analyze the specificity of the effect of 1H4, the association of PP1 with the cellular regulatory subunits, NIPP1 and PNUTS, was analyzed compared to the association with Tat. PP1 was precipitated on microcystin-sepharose from cell lysates and the precipitated proteins were trypsinized and analyzed by LC-MS/MS spectrometry. 293T cells were transfected with Flag-tagged Tat. PP1 was precipitated with microcystin agarose. The associated proteins were trypsinized and analyzed by nano-LC MS/MS. Liquid chromatography peak amplitudes for specific peptides derived from Tat (551.95 Da), PP1α (500.78 Da), NIPP1 (501.77 Da) and PNUTS (110.88 kDa) are shown. The peptides were identified through MS/MS sequencing analysis by SEQUEST. FIG. 6B shows the relative amounts of Tat and PP1 subunits PNUTS and NIPP1 in different experiments. Normalization Level (NL) or the amplitude of MS peak signal was used as a value proportional to sample amount. First, the specific peptides were detected by SEQUEST. Then the exact mass and Retention Time of the peptides were used to filter the LC data. As previously shown, the LC-MS peak area could be used for sample amount quantification in a wide range of sample concentrations (Chelius, D. and P. V. Bondarenko, *Quantitative profiling of proteins in complex mixtures using liquid chromatography and mass spectrometry*. J Proteome Res, 2002. 1(4): p. 317-23). The data was measured in the linear range of the NL signal. FIG. 6B represents the amplitude of the LC peak for specific peptides of the following proteins: Tat (peptide RAPQDSQTHQASLSK, SEQ ID NO: 8, m/z=551.95 Da, z=3+), PNUTS (peptide GPQGPGGGGIN-VQEILTSIMGSPNSHPSEELLK, SEQ ID NO: 9, m/z=1100.88 Da, z=3+), NIPP1 (peptide VFLIDLNSTH-GTFLGHIR, SEQ ID NO: 10, m/z=510.77 Da, z=4+) and PP1α (peptide LNLDSIIGR, SEQ ID NO: 11, m/z=500.78, z=2+). The amplitude of the signal was normalized for each peptide to its maximum on the samples set. PNUTS and NIPP1 were equally associated with PP1 in mock-transfected, Tat-transfected and Tat-transfected cells treated with 1H4 (FIG. 6B). In contrast, Tat association was reduced in the Tat-transfected cells that were treated with 1H4 (FIG. 6B). Therefore, 1H4 affected the interaction of PP1 with Tat without any effect on the interaction of PP1 with PNUTS or NIPP1.

1H4 has No Effect on the Expression of Cellular Proteins.

To determine if 1H4 has a negative effect on protein expression profiles, the global cellular proteome was analyzed by mass spectrometry. Protein expression was analyzed in 293T cells untreated or treated with 1H4. The 293T cells were treated with 10 μM 1H4 for 18 h or untreated and lysed. Lysates were trypsinized, fractionated by ion-exchange chromatography and then analyzed on by LC-MS-MS using C18 column. MS-MS data were analyzed by SEQUEST. Expression of 1722 proteins was detected in the untreated sample and 1739 proteins in the 1H4-treated sample. The 28 major proteins having highest score in SEQUEST are shown in FIG. 7. Analysis of the 28 proteins having the highest Scores in SEQUEST search showed very close score (credibility of search result) and coverage (part of the database protein sequence found experimentally) (FIG. 7) indicating that 1H4 treatment did not significantly change the cellular proteome.

1H4 Prevents Tat-Mediated PP1 Translocation to the Nucleus.

Figure 8:
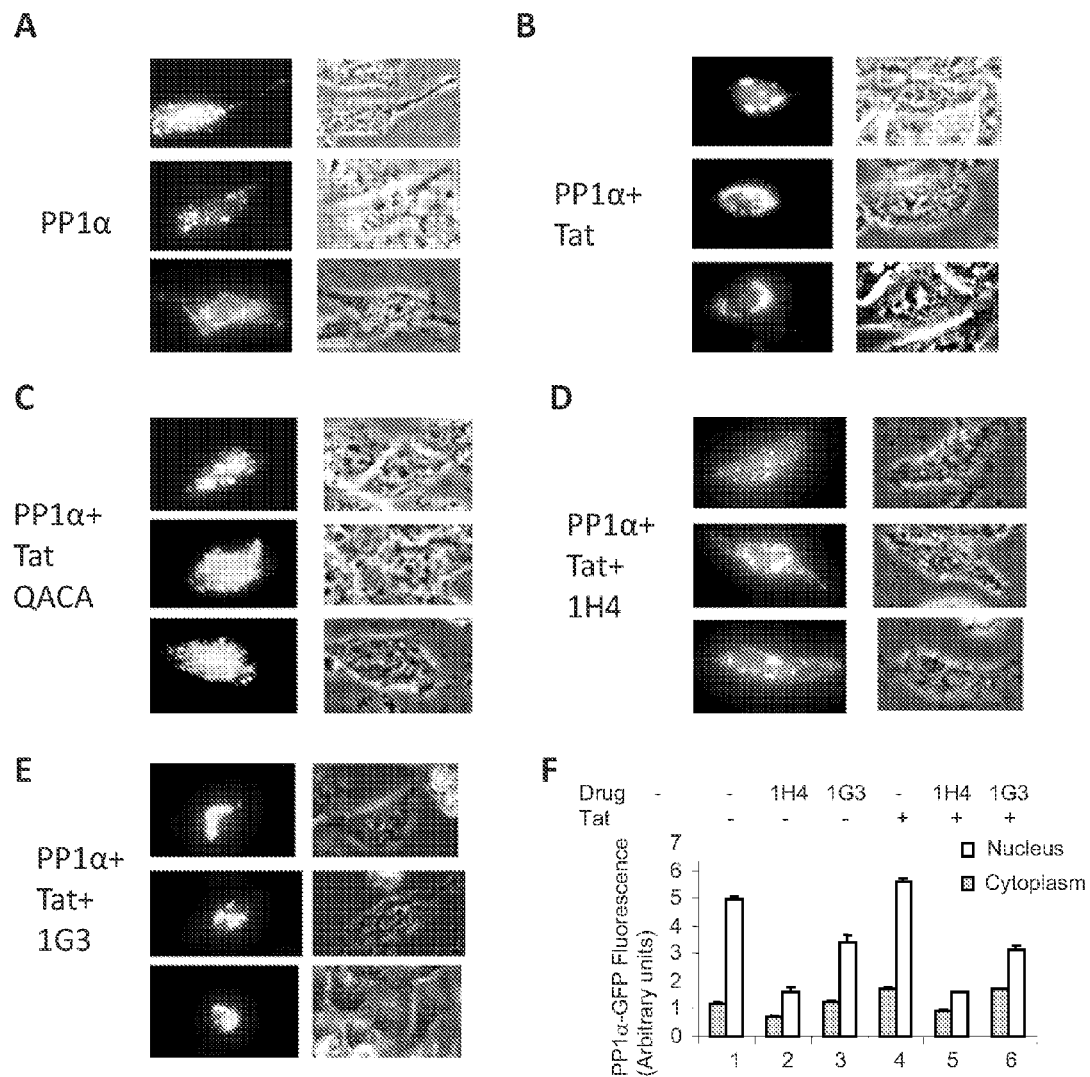

In live cells, PP1α is dynamically distributed between the cytoplasm and the nucleus, and its shuttling into the nucleus is thought to be regulated by its interaction with sds22 and inhibitor-3 regulatory subunits (Lesage, B., et al., *A complex of catalytically inactive protein phosphatase-1 sandwiched between Sds22 and inhibitor-3*. Biochemistry, 2007. 46(31): p. 8909-19). HIV-1 Tat facilitates nuclear localization of PP1α via an effect that requires the intact QVCF sequence of Tat. The effect of 1H4 on Tat-driven nuclear localization of PP1α in HeLa cells that were transfected with Flag-Tat and PP1α-EGFP expression vectors and treated with 1H4 or a control compound for 18 hrs was analyzed. HeLa cells were transfected with PP1α-EGFP (PP1α) (A), PP1α-EGFP and WT Flag-Tat (B, D and E) or PP1α-EGFP and Flag-Tat 35QACA38 mutant (C) and treated with 10 μM 1H4 (D) or control 1G3 compound (E) for 18 hours. The cells were photographed on Olympus IX51 using a blue filter for EGFP fluorescence or phase contrast with 400× magnification. F, 293T cells were transfected with PP1α-EGFP or PP1α-EGFP and Tat expression vectors. At 24 hrs posttransfection cells were lysed in low salt buffer and cytoplasmic extract was separated from the nuclear material by centrifugation. Fluorescence was measured in the nuclear and cytoplasmic fractions using Perkin-Elmer Luminoscan. In untreated cells, PP1α was mainly localized to the cytoplasm (FIG. 8A). This was changed to a more pronounced nuclear and perinuclear localization when Tat was co-expressed with PP1α (FIG. 8B). Mutant Tat $^{35}$QACA$^{38}$ did not cause such changes in PP1α localization (FIG. 8C). Treatment with 1H4 drastically diminished nuclear localization of PP1α in the presence of Tat (FIG. 8D). In contrast, treatment with the inactive compound 1G3 did not reduce the nuclear PP1α localization in the presence of Tat (FIG. 8F). To achieve quantifiable results, fluorescence of PP1α-EGFP in nuclear and cytoplasmic fractions of 293T cells that were transfected with PP1α-EGFP or PP1α-EGFP and Tat expression vectors and treated with 1H4 was measured. The cytoplasmic and nuclear fractions were separated as described in Materials and Methods. Analysis of EFGP fluorescence showed a significant decrease of nuclear PP1α-EGFP in the 1H4-treated cells compared to the untreated controls or the cells treated with 1G3 compound (FIG. 8F). Unexpectedly, this was observed both in the absence and the presence of Tat (FIG. 8F). Taken together, the experiments showed that a small molecular mimetic of the RVxF motif efficiently inhibited HIV-1 transcription apparently by disrupting the interaction of Tat with PP1 and affecting the cellular distribution of PP1.

Optimization of the 1H4 Compound.

Figure 9:
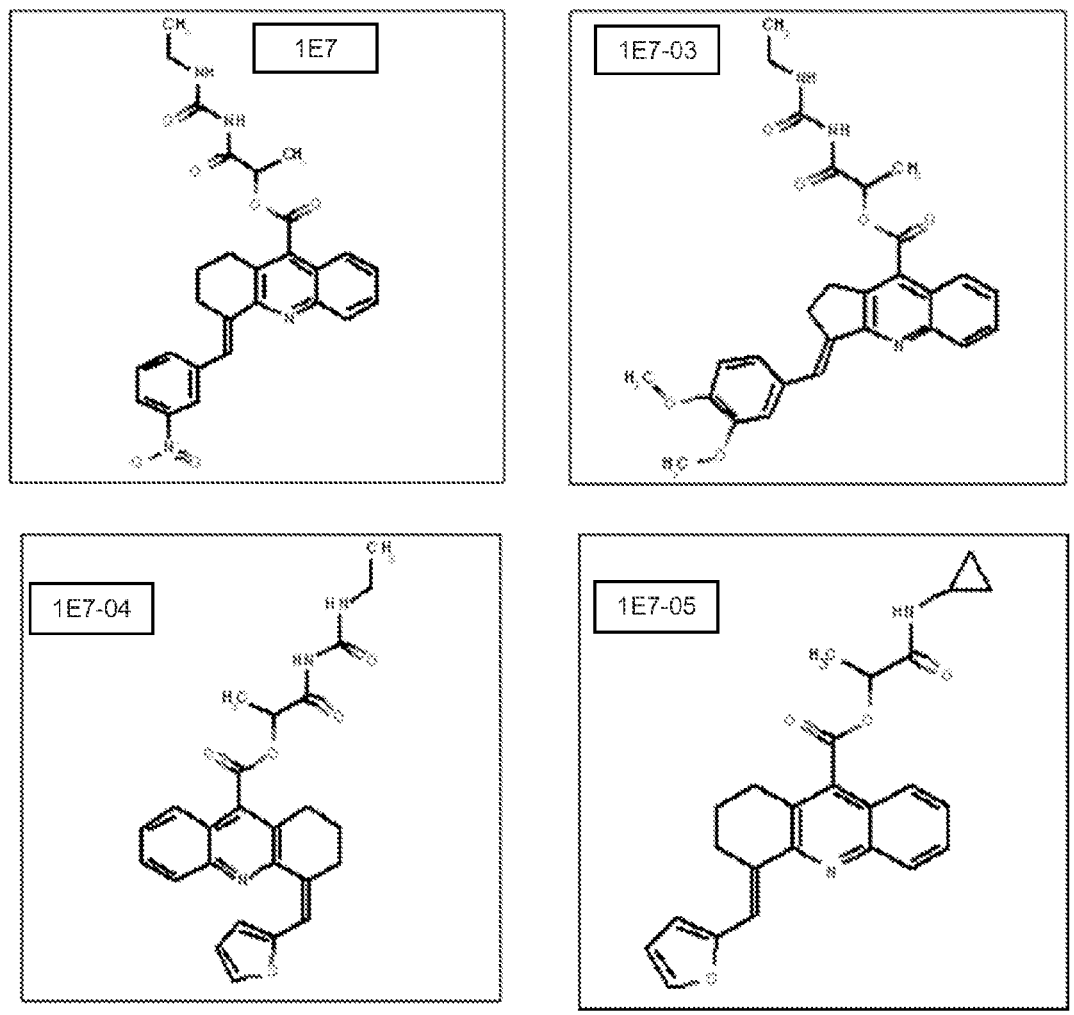

Optimization continued of the 1H4 compound by creating a targeted library based on the 1H4 structure. The library was screened using the CEM-GFP cells infected with Ad-Tat, or 293T cells transiently transfected with HIV-1 LTR reporter and Tat expression vectors. A new compound, 1E07 was identified that inhibited HIV-1 transcription in CEM GFP cells 2.5-times greater, but also exhibited higher toxicity in T cells (Table 2 and FIG. 9). We next created and screened a library based on the 1E7 compound. As a result, another compound, 1E7-03, was identified that was equally potent as 1E7 in HIV-1 transcription inhibition in 293T cells, and was more potent than the 1H4 (Table 2 and FIG. 9). Neither of the compounds was toxic below 30 μM concentrations.

TABLE 2

Optimization of the 1H4 compound.

| ID | Inhibition Tat-induced HIV transcription in CEM cells, IC$_{50}$ | Inhibition Tat-induced HIV transcription in 293T cells, IC$_{50}$ | 50% Inhibition of HIV-1 replication | Toxicity in CEM cells, IC$_{50}$ |
|---|---|---|---|---|
| 1H04 | 10 μM | 5 μM | 10 μM | 30 μM |
| 1E07 | 4 μM | 4 μM | 3 μM | 10 μM |
| 1E7-03 | | | 3 μM | >20 μM |
| 1E7-04 | | | 3 μM | 7 μM |

The initial screening of the 1H4-based library resulted in identification of the 1E07 compound. A subsequent screening of 1E07-based library resulted in identification of the 1E7-03 compound.

Example 2

Inhibition of Ebola Virus Replication by PP1-Targeted Compounds

Figure 10:
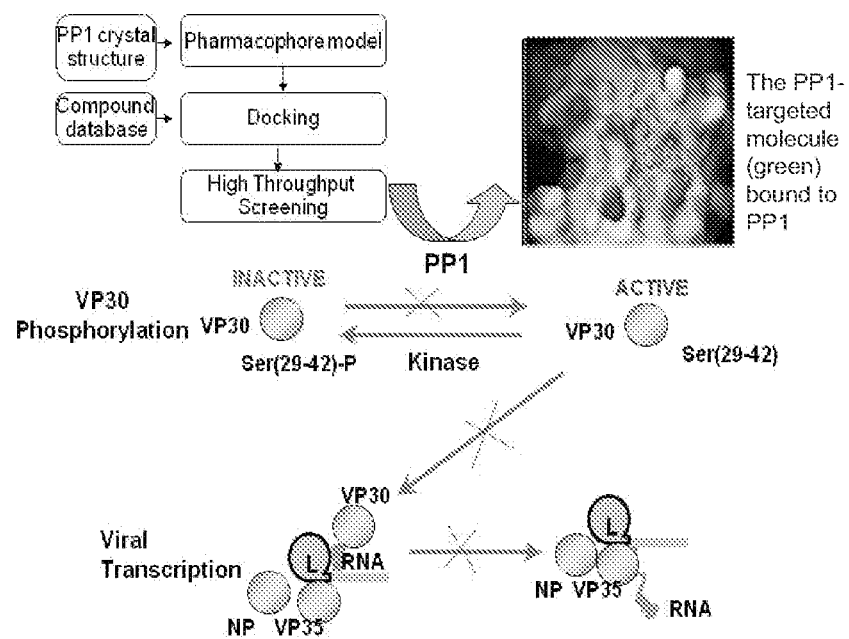

The PP1-targeted, small-molecule compounds (FIG. 9) that target a non-catalytic site in PP1 were utilized. It was thought that if the compounds can be used to block the interaction of EBOV VP30 with PP1, the viral protein will remain phosphorylated and therefore the viral polymerase will remain in the transcriptionally inactive form (FIG. 10). As a result, replication of the virus will be blocked.

Figure 11:
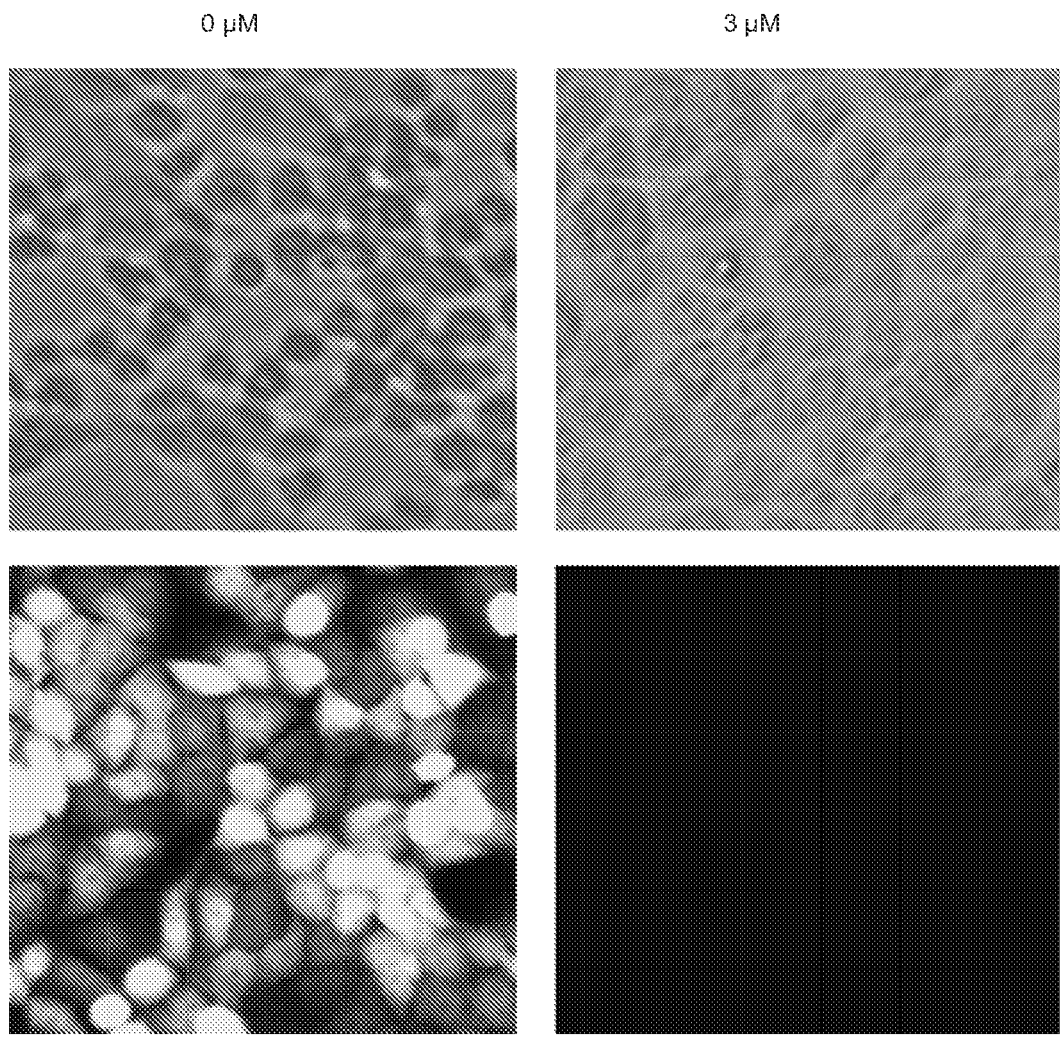

Four of the molecules, 1E7, 1E7-03, 1E7-04, and 1E7-05 (FIG. 9) were selected to test their activity against EBOV in cell culture. The experiments were performed in the BSL-4 laboratory at the University of Texas Medical Branch (UTMB) and the Galveston National Laboratory. A single dose of the compounds at 1, 3 or 10 μM concentrations were added to supernatants of Vero-E6 cell monolayers. 30 minutes later, the monolayers were infected with a recombinant EBOV expressing eGFP (EBOV-eGFP), available in the UTMB/GNL World Reference Collection of Emerging Viruses and Arboviruses, at a multiplicity of infection (MOI) 0.001 PFU/cell. This was followed by daily examinations of eGFP fluorescence produced by the recombinant EBOV, and daily collections of medium aliquots followed by plaque titration of the released virus present in the aliquots. The infection resulted in high viral titers in the medium, and a visible green fluorescence of various intensities in 95% of the cells starting on day 3 (data for 1E7-03 shown in FIG. 11). The three tested compounds, 1E7, 1E7-04 (not shown), and 1E7-05 (not shown), were highly potent in inhibiting EBOV but demonstrated some toxicity. However, compound 1E7-03 completely suppressed EBOV replication (FIG. 11) without any detectable cytotoxicity. The inhibitory effect was observed up to 7 days post-infection in several independent experiments.

Figure 12:
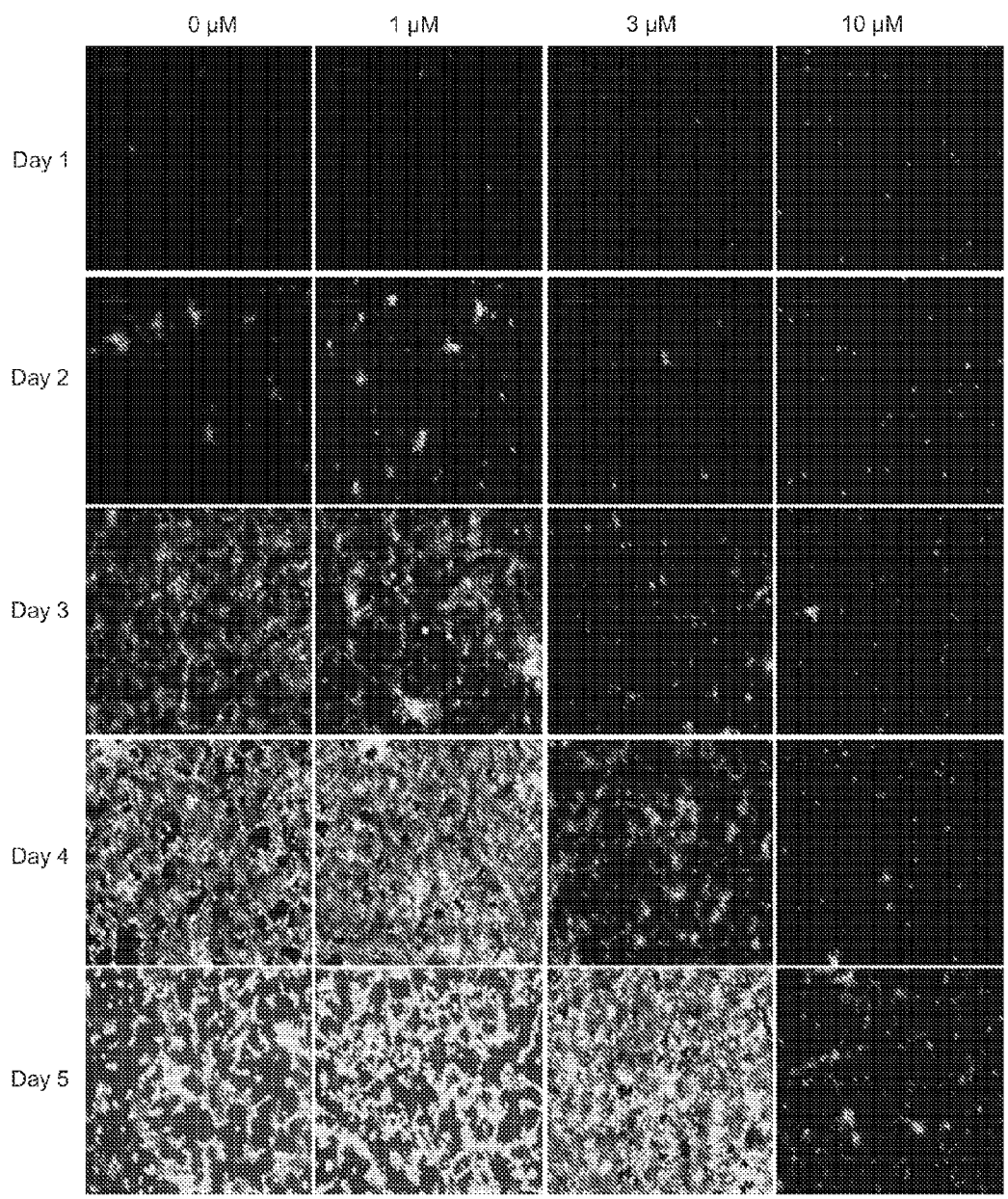
Figure 13:
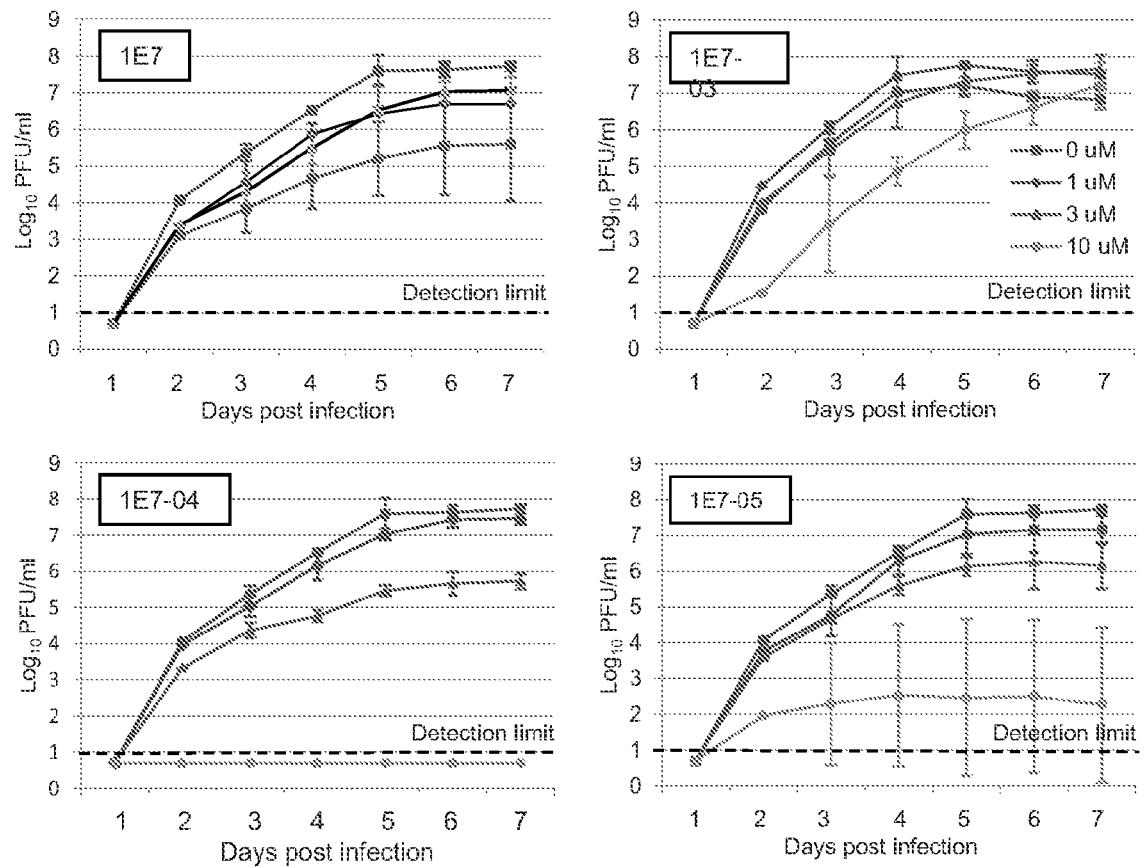

In the next experiment, infection with MOU 0.01 PFU was tested, and the compounds were added at the time of infection at the same concentrations as in the previous experiment. To measure replication of EBOV, UV microscopy pictures and aliquots of medium were taken for titration of the virus every 24 hours. UV and bright field microscopy demonstrated a strong dose-dependent inhibition of EBOV replication by all four compounds (data for 1E7-03 shown in FIG. 12). Again, 1E7, 1E7-04, and 1E7-05 demonstrated a visible toxicity resulting in a partial destruction of the cell monolayer. Consistently with the previous experiment, no toxicity was observed for the 1E7-03 compound. Titration of the viral aliquots demonstrated a dose-dependent reduction of the viral titers in supernatants of cells treated with each compound (FIG. 13). For example, addition of 1E7-03 at 10 μM resulted in the reduction of the viral titers on days 2 and 3 by 200 and 147-fold, respectively.

Figure 14:
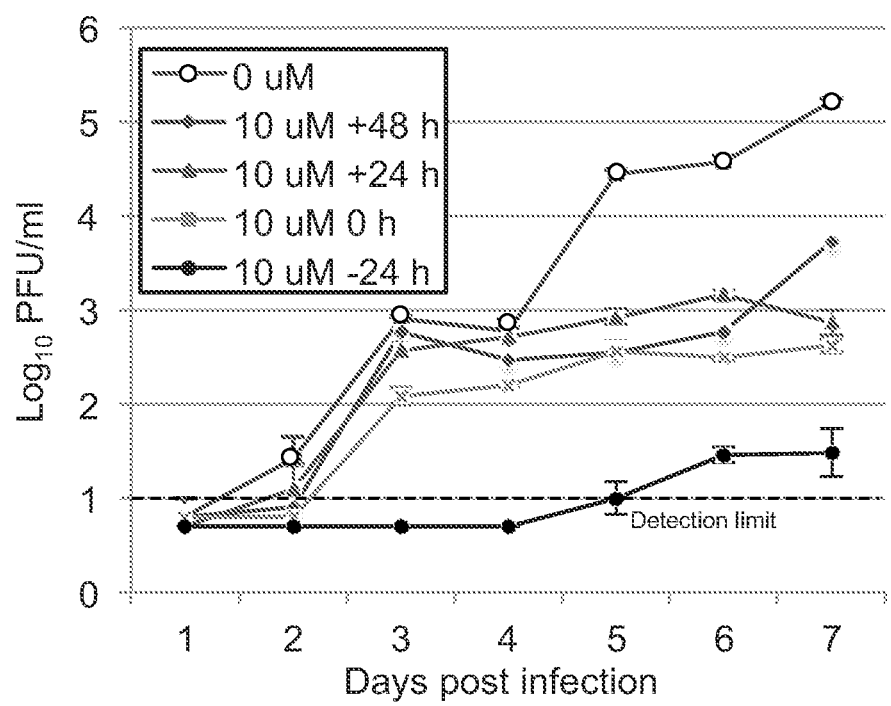

In the next set of experiments, the compound 1E7-03 was further analyzed, which did not demonstrate toxicity at the concentrations tested. To determine the effect of the time of addition of the compound, 1E7-03 was added at 10 μM 24 hours prior to the infection, during the infection, or 24 or 48 hours post infection with EBOV-eGFP at MOI 0.01 PFU/cell, and medium aliquots were taken every 24 hours. The daily UV microscopic examinations (not shown) and titration of the collected aliquots demonstrated that each treatment resulted in inhibition of EVOV-eGFP replication (FIG. 14). Addition of the compound at 24 hours prior to infection resulted in the lack of any detectable virus in the medium up to four days after infection and very low viral titers on the subsequent days; for example, on days 3 and 7 post infection, the relative reduction of the viral titers was >118 and 11,507-fold, respectively. Adding the compound at 0, 24, or 48 hours post infection resulted in reductions of the viral titers on day 3 of 77, 33 and 79-fold, respectively, and on day 7 reductions of 950, 491, and 166-fold respectively (FIG. 14).

Figure 15:
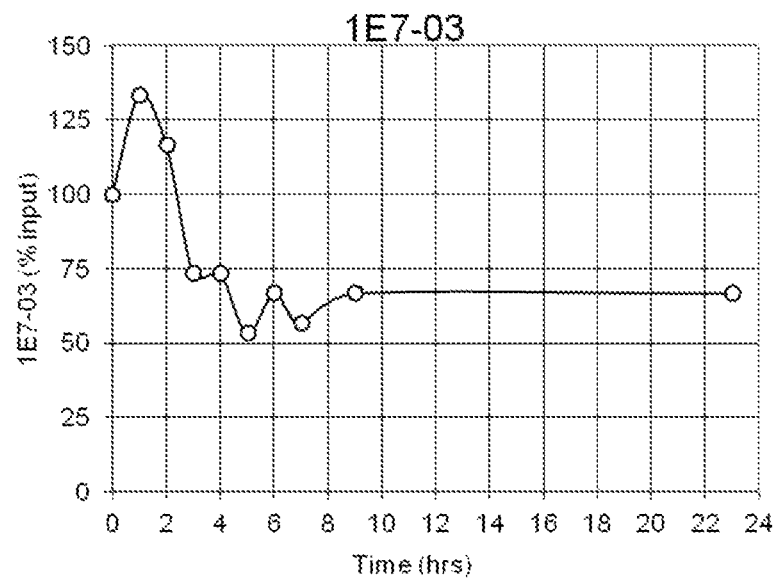
Figure 16:
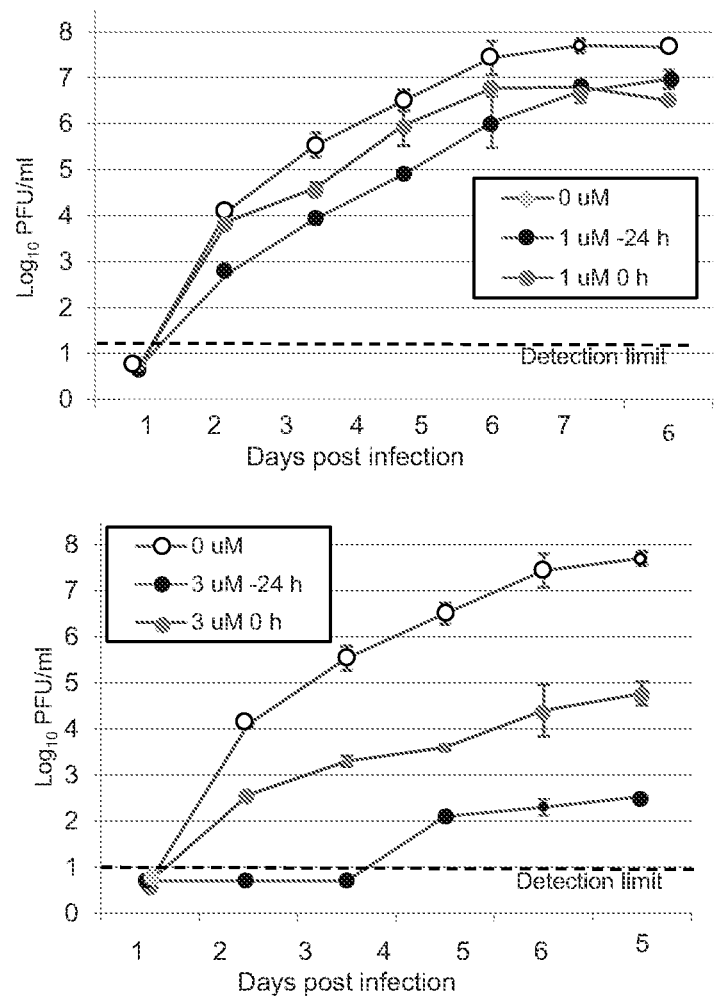

Next the stability of 1E7-03 compound in water solution was tested. The compound was dissolved at 1 µM concentration and incubated up to 24 hrs (FIG. 15). It was found that starting 3 hours after addition of the compound, its concentration in solution was sharply reduced by about 25% (FIG. 15). Because of the sharp reduction of the concentration of the compound, the effect of its addition every 24 hours at 1 µM or 3 µM was tested, with the first dose added starting at 24 hours prior to the infection or during the infection. Aliquots of the medium were taken daily, and EBOV-eGFP was titrated (FIG. 16). It was found that each regiment of treatment resulted in a reduced replication of the virus with greater effects observed with 3 µM; consistently with the previous experiment (FIG. 16) adding the component starting at 24 hours prior to infection resulted in the strongest inhibition. For example, at 3 µM no virus was detected up to 3 days post infection, which corresponds to >68,129-fold reduction of the viral titers; on days 4, 5, 6, the relative reduction of the viral titers was 25,119; 135,936; and 146,789-fold (FIG. 16).

Figure 17:
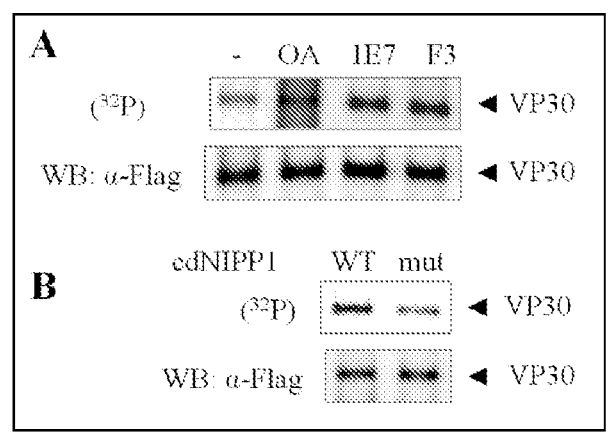

The effect of the 1E7-03 compound on EBOV VP30 phosphorylation was next analyzed by expressing Flag-tagged VP30. The cells were treated with the indicated compounds or okadaic acid and then pulsed with ($^{32}$P) orthophosphate for 3 hrs. Phosphorylation of VP30 was increased by okadaic acid treatment as expected and also dramatically (2.7 fold) increased by 1E7-03 or an additional PP1-targeting F3 compound (FIG. 17A). Co-expression of VP30 with cdNIPP also increased its phosphorylation (FIG. 17B) suggesting that PP1 dephosphorylates VP30 in vivo.

Figure 18:
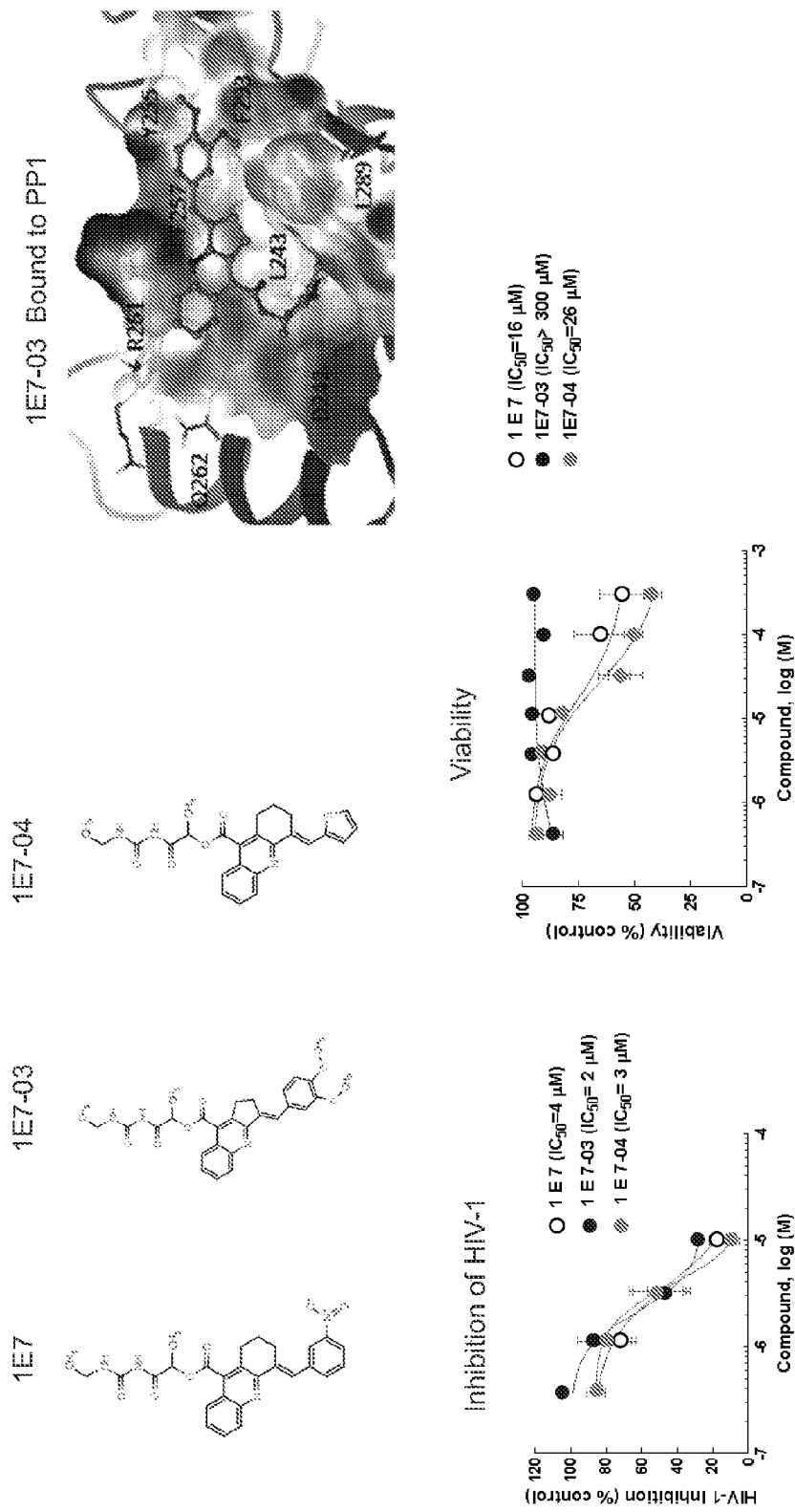

The effect of 1E7-03 compound on HIV-1 inhibition and cell viability was measured in FIG. 18. The graphs indicate that 1E7-03 is a potent HIV-1 inhibitor and maintains the most viability in control cell viability assays. FIG. 18 also illustrates the PP1 binding mode for 1E7-03 positioned near amino acid residues of PP1 capable of bonding with 1E7-03.

The effect of 1E7-03 compound on cellular distribution of PP1 was analyzed in FIG. 19. Fluorescence was measured in the nucleus and cytoplasm fractions. The photographs show that 1E7-03 inhibited the translocation of Tat and PP1 into the nucleus.

Figure 20:
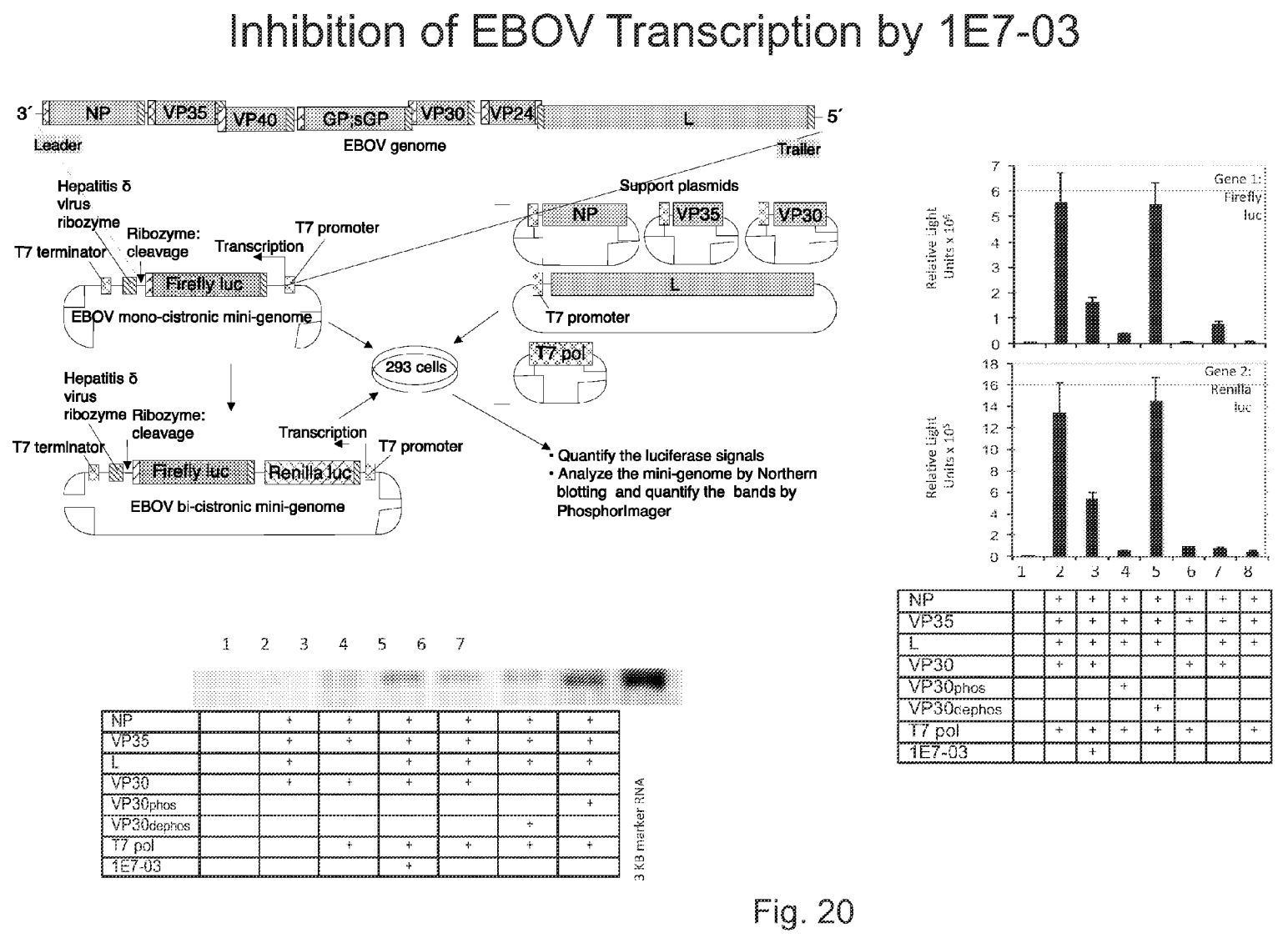

The effect of the 1E7-03 compound on EBOV transcription was analyzed using a mini-genome assay in FIG. 20. An altered Ebola-virus replicon system for evaluating anti-Ebola transcriptional activity was used. Mini-genome assay was achieved by the use of support plasmids, where transcription is measured by levels of reporter luciferase expression signals and Northern blotting wherein the bands are quantified by PhosphorImaging. All of these measurements show that 1E7-03 inhibits EBOV transcription.

These data point to a much greater potency of the compound when compared to the five drugs with demonstrated anti-viral effect against EBOV, which are aimed at inhibition of EBOV entry: (Basu, A., et al., *Identification of a small-molecule entry inhibitor for filoviruses*. J Virol, 2011. 85(7): p. 3106-19), heat shock protein 90 (Smith, D. R., et al., *Inhibition of heat-shock protein 90 reduces Ebola virus replication*. Antiviral Res, 2010. 87(2): p. 187-94), of virus-cell fusion (Wolf, M. C., et al., *A broad-spectrum antiviral targeting entry of enveloped viruses*. Proc Natl Acad Sci USA, 2010. 107(7): p. 3157-62), an unknown, conserved host pathway (Aman, M. J., et al., *Development of a broad-spectrum antiviral with activity against Ebola virus*. Antiviral Res, 2009. 83(3): p. 245-51), and the endosomal membrane protein Niemann-Pick C1 (Cote, M., et al., *Small molecule inhibitors reveal Niemann-Pick C1 is essential for Ebola virus infection*. Nature, 2011).

What is claimed is:

1. A method for treating a subject infected with or at risk of infection with Ebola, the method comprising administering to a subject in need of such treatment a therapeutically effective amount of a compound of formula (I) comprising:

(I)

wherein n is 1 or 2;
Ar is phenyl or thienyl, and is optionally substituted;
each $R^1$ is independently $R^6$, $C(O)R^6$, $C(O)$—$OR^6$, or $C(O) N(R^6)_2$;
$R^2$ is H or optionally substituted C1-C6 alkyl, or a group of formula —C(O)NH—$R^1$;
$R^3$ is independently at each occurrence selected from halo, $NO_2$, CN, R, OR, $NR_2$;
$S(O)_qR$, COOR, and $CONR_2$, where each R is independently H, C1-C4 alkyl, or C1-C4 haloalkyl;
m is 0-4;
$R^4$ is $R^6$, halo, =O, $COOR^6$, $CON(R^6)_2$, $S(O)_qR^6$, $N(R^6)_2$, or $OR^6$;
p is 0-2;
each q is independently 0-2;
Z is O or $NR^5$;
$R^5$ is $R^6$ or $C(O)R^6$; and
$R^6$ is independently at each occurrence selected from H, C1-C6 alkyl, C5-C6 aryl, and (C5-C6-aryl)-C1-C6 alkyl, where each alkyl and aryl is optionally substituted;
provided that n is 2 when Z is O and Ar represents para-halophenyl;
or a pharmaceutically acceptable salt thereof.

2. The method of claim 1, comprising a pharmaceutically acceptable salt of a compound of formula I.
3. The method of claim 1, wherein Z is O.
4. The method of claim 1, wherein n is 1.
5. The method of claim 1, wherein n is 2.
6. The method of claim 1, wherein $R^2$ is H or C1-C4 alkyl.
7. The method of claim 1, wherein Ar is optionally substituted phenyl.
8. The method of claim 1, wherein Ar is optionally substituted 2-thienyl.
9. The method of claim 1, wherein Ar is optionally substituted 3-thienyl.
10. A method to inhibit replication of Ebola virus, comprising contacting the Ebola virus or a cell containing the Ebola virus with a compound of formula (I).
11. A method for treating a subject infected with or at risk of infection with Ebola, the method comprising administering to a subject in need of such treatment a therapeutically effective amount of a compound selected from the group consisting of Compound A Compound B Compound C Compound D Compound E
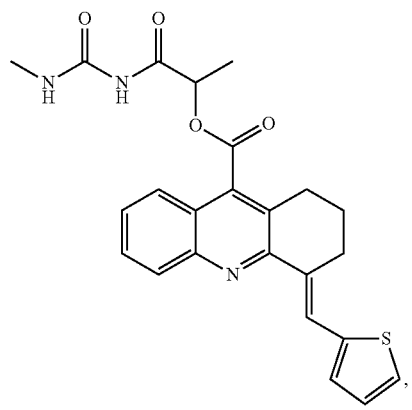
Compound 1H4
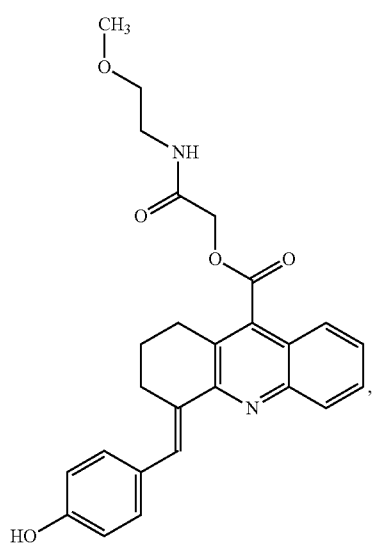
Compound 1G3
Compound 1C7
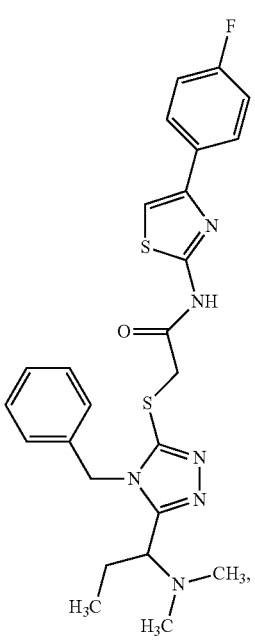
Compound 3C8
1E7-03
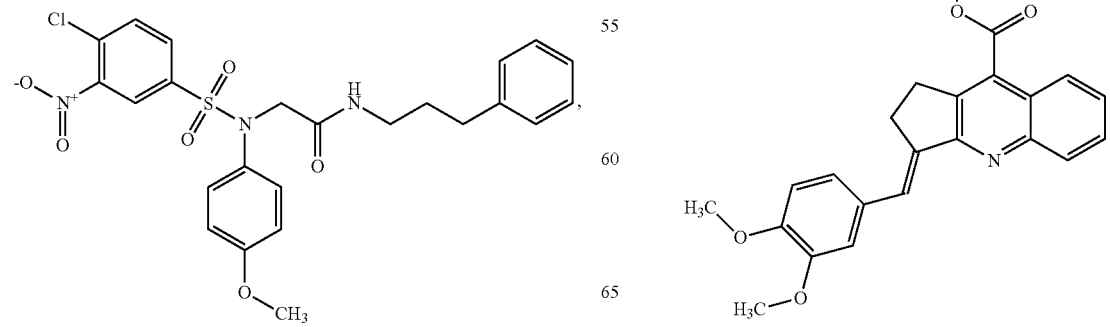

-continued
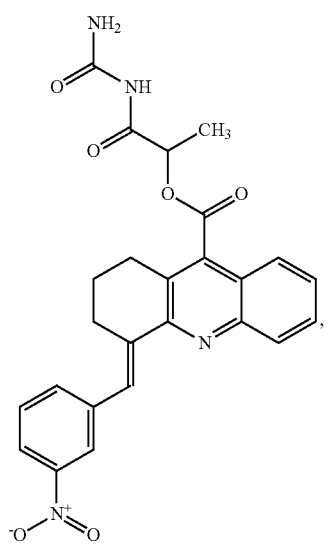
1E7-01
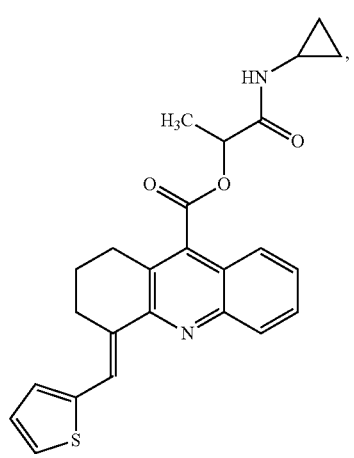
1E7-05
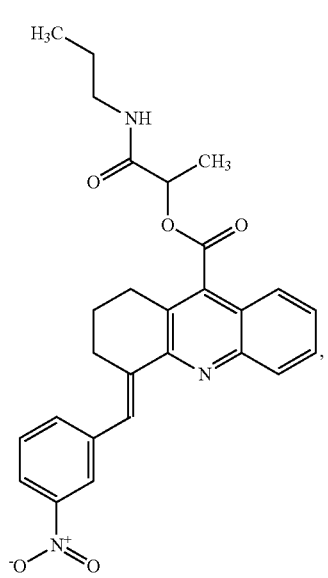
1E7-02
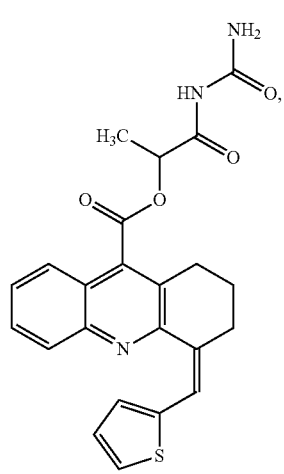
1E7-06
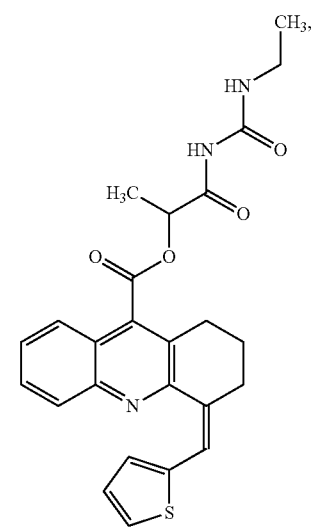
1E7-04
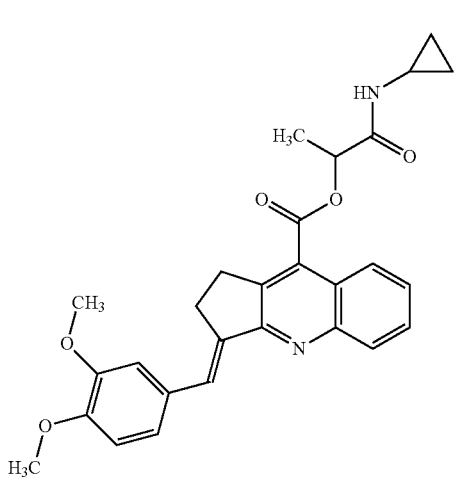
1E7-07

-continued

1E7-08
[chemical structure]

1E7-09
[chemical structure]

1E7-10
[chemical structure]

and pharmaceutically acceptable salts of these compounds.

12. A method for inhibiting replication of Ebola virus, comprising contacting the Ebola virus or a cell containing the Ebola virus with a compound selected from the group consisting of Compound A
[chemical structure]

Compound B
[chemical structure]

Compound C
[chemical structure]

-continued
Compound D
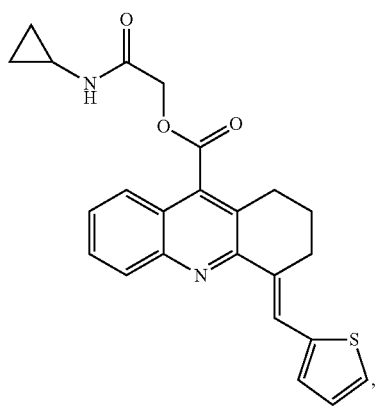
Compound 1G3
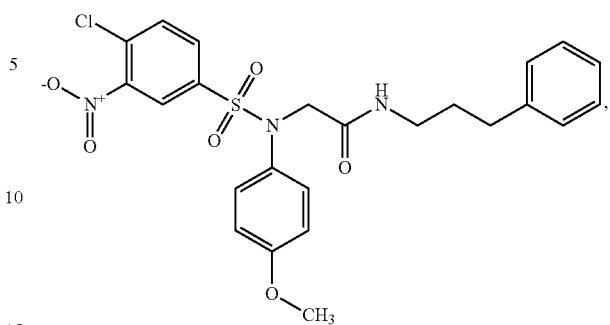
Compound E
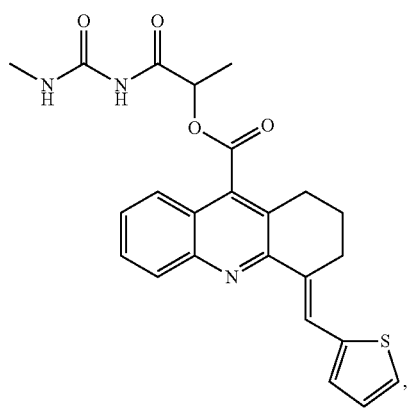
Compound 1C7
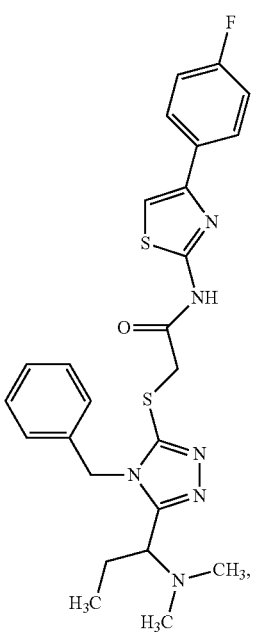
Compound 1H4
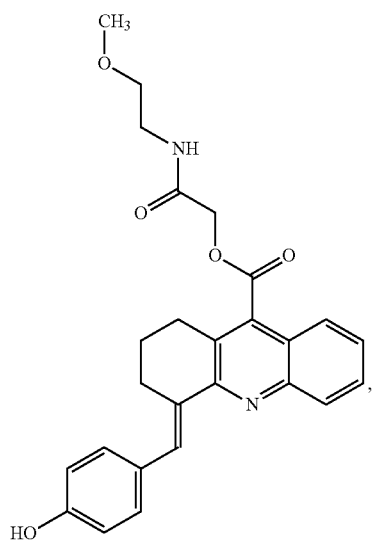
Compound 3C8
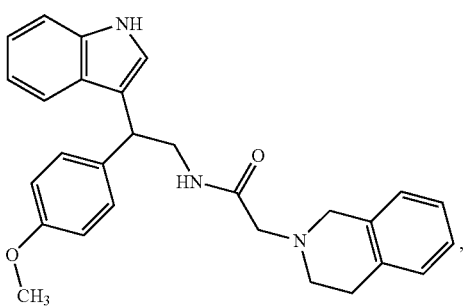

1E7-03
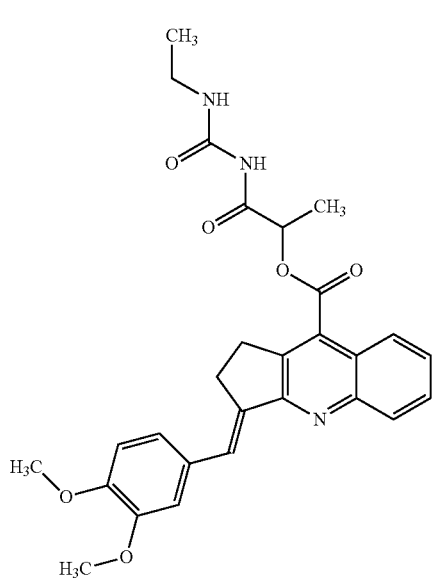
1E7-01
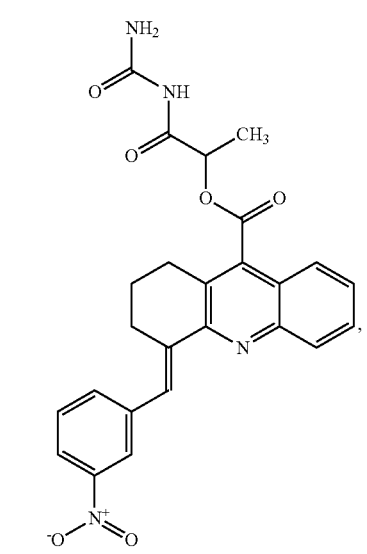
1E7-02
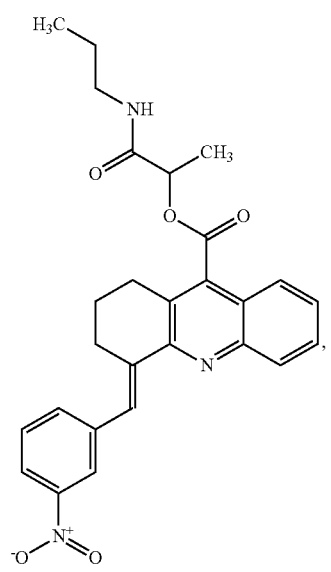
1E7-04
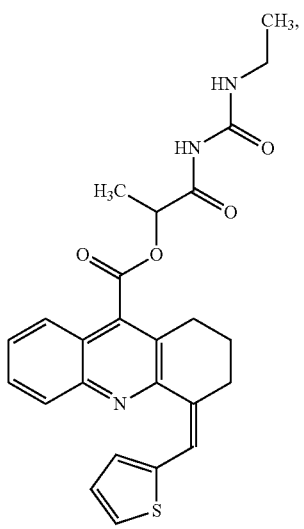
1E7-05
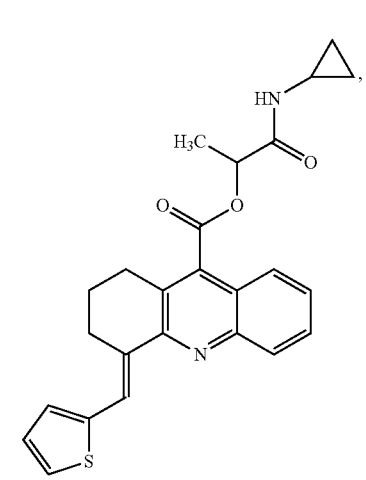
1E7-06
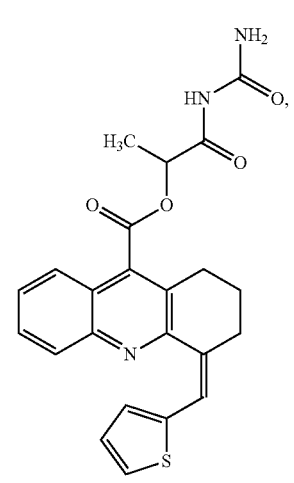

-continued
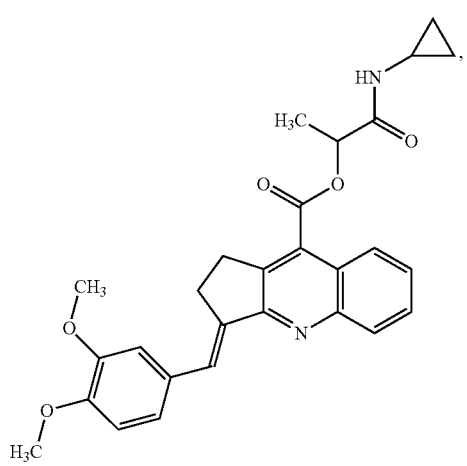
1E7-07
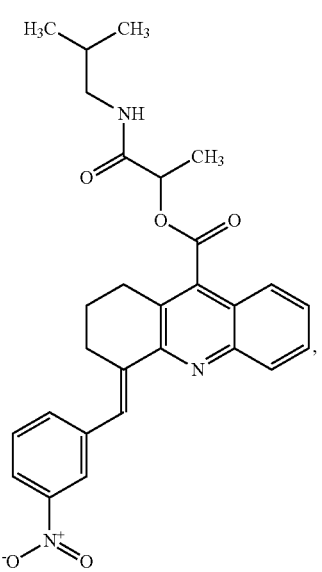
1E7-08
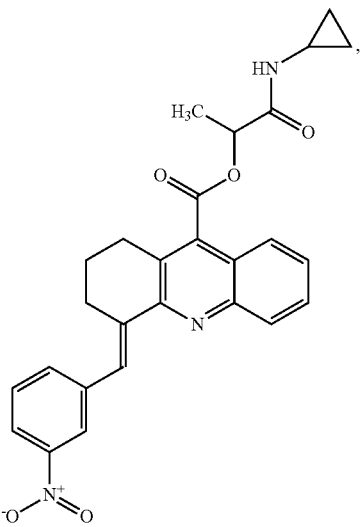
1E7-09
1E7-10
and pharmaceutically acceptable salts of these compounds.
* * * * *

UNITED STATES PATENT AND TRADEMARK OFFICE
CERTIFICATE OF CORRECTION

| | |
|---|---|
| PATENT NO. | : 9,447,047 B2 |
| APPLICATION NO. | : 14/421757 |
| DATED | : September 20, 2016 |
| INVENTOR(S) | : Sergei Nekhai et al. |

It is certified that error appears in the above-identified patent and that said Letters Patent is hereby corrected as shown below:

In the Specification

At Column 1, after Line 11, please insert --GOVERNMENT INTEREST:
GOVERNMENT LICENSE RIGHTS (1) This invention was made with government support under RR003048, and HL003679 awarded by the National Institutes of Health. The government has certain rights in the invention.--

Signed and Sealed this
Twenty-second Day of August, 2023

*Katherine Kelly Vidal*

Katherine Kelly Vidal
*Director of the United States Patent and Trademark Office*